US012004782B2

(12) United States Patent
Butler et al.

(10) Patent No.: US 12,004,782 B2
(45) Date of Patent: Jun. 11, 2024

(54) INSTRUMENT FOR LOCKING ORTHOPEDIC SCREWS

(71) Applicant: Warsaw Orthopedic, Inc., Warsaw, IN (US)

(72) Inventors: Brian A. Butler, Atoka, TN (US); Aubrey R. Mills, Memphis, TN (US); Christel Italiaie, Memphis, TN (US); Bret M. Wilfong, Hernando, MS (US); Madeline G. Wilson, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 656 days.

(21) Appl. No.: 17/167,258

(22) Filed: Feb. 4, 2021

(65) Prior Publication Data
US 2021/0298794 A1    Sep. 30, 2021

Related U.S. Application Data

(63) Continuation-in-part of application No. 16/830,377, filed on Mar. 26, 2020, now Pat. No. 11,730,529.

(51) Int. Cl.
*A61B 17/70* (2006.01)
*A61B 17/56* (2006.01)
*A61B 17/88* (2006.01)

(52) U.S. Cl.
CPC ...... *A61B 17/7082* (2013.01); *A61B 17/8886* (2013.01); *A61B 2017/564* (2013.01); *A61B 17/7032* (2013.01); *A61B 17/7074* (2013.01); *A61B 17/7076* (2013.01); *A61B 17/7085* (2013.01); *A61B 17/7086* (2013.01);

(Continued)

(58) Field of Classification Search
CPC ............ A61B 17/7082; A61B 17/7032; A61B 17/8886; A61B 17/083; A61B 17/7074; A61B 17/7076; A61B 17/7085; A61B 17/7086; A61B 17/7088; A61B 17/7091; A61B 17/8875; A61B 2017/564
USPC ........ 606/104, 264–275, 278, 279, 86 R, 87, 606/96–99, 86 A, 914
See application file for complete search history.

(56) References Cited

U.S. PATENT DOCUMENTS

| 4,098,351 A | 7/1978 | Alessio |
|---|---|---|
| 6,415,693 B1 | 7/2002 | Simon et al. |
| 6,497,166 B1 | 12/2002 | Fleckenstein |

(Continued)

*Primary Examiner* — Marcela I. Shirsat
(74) *Attorney, Agent, or Firm* — FOX ROTHSCHILD LLP

(57) ABSTRACT

Systems, instruments, and methods for operating a surgical instrument are disclosed. The instrument may include a drive shaft axially aligned with a central axis of the surgical instrument. The drive shaft may include a first mating end and be rotatably supported within a drive housing having a contoured interior supporting the first mating end. The instrument may include an outer shaft having an outer receiver interface configured to selectively couple and uncouple to a connecting portion of a receiver. The instrument may also include a plunger that is axially aligned with the central axis and having a second mating end disposed within the contoured interior of the drive housing. In various embodiments, the second mating end may be axially aligned with and in contact with the first mating end. In various embodiments, the plunger may be configured to linearly translate along the central axis upon rotation of the drive shaft.

17 Claims, 21 Drawing Sheets

(52) U.S. Cl.
CPC ....... *A61B 17/7088* (2013.01); *A61B 17/7091* (2013.01); *A61B 17/8875* (2013.01)

(56) References Cited

U.S. PATENT DOCUMENTS

| | | | |
|---|---|---|---|
| 6,857,343 B1 | 2/2005 | Easterbrooks et al. |
| 7,226,453 B2 | 6/2007 | Chao et al. |
| 7,572,264 B2 | 8/2009 | Null et al. |
| 7,771,459 B2 | 8/2010 | von Oepen |
| 7,846,167 B2 | 12/2010 | Garcia et al. |
| 7,947,047 B2 | 5/2011 | Arnal |
| 7,988,699 B2 | 8/2011 | Martz et al. |
| 8,048,124 B2 | 11/2011 | Chin et al. |
| 8,100,916 B2 | 1/2012 | Kumar et al. |
| 8,221,431 B2 | 7/2012 | Chenaux |
| 8,231,635 B2 | 7/2012 | Sharifi-Mehr et al. |
| 8,262,670 B2 | 9/2012 | Laubert et al. |
| 8,343,165 B2 | 1/2013 | Berrevoets |
| 8,394,108 B2 | 3/2013 | McLean et al. |
| 8,459,155 B2 | 6/2013 | Canizares, Jr. et al. |
| 8,460,307 B2 | 6/2013 | Saidha et al. |
| 8,475,466 B2 | 7/2013 | Chenaux |
| 8,540,756 B2 | 9/2013 | Olsen et al. |
| 8,747,411 B2 | 6/2014 | Mitchell |
| 8,757,035 B2 | 6/2014 | Kerboul et al. |
| 8,763,499 B2 | 7/2014 | Dahners |
| 8,784,431 B1 | 7/2014 | Harder et al. |
| 8,806,973 B2 | 8/2014 | Ross et al. |
| 8,845,652 B2 | 9/2014 | Heinz |
| 8,882,775 B2 | 11/2014 | LaPosta et al. |
| 8,900,248 B2 | 12/2014 | Biyani |
| 8,900,280 B2 | 12/2014 | Paroth et al. |
| 8,932,303 B2 | 1/2015 | Bouliane |
| 8,945,193 B2 | 2/2015 | Kirschman |
| 8,951,264 B2 | 2/2015 | Saidha et al. |
| 8,968,276 B2 | 3/2015 | Zemlok et al. |
| 8,992,587 B2 | 3/2015 | Kirschman |
| 8,998,921 B2 | 4/2015 | Sharifi-Mehr et al. |
| 9,017,333 B2 | 4/2015 | Beale et al. |
| 9,055,943 B2 | 6/2015 | Zemlok et al. |
| 9,113,976 B2 | 8/2015 | Yevmenenko et al. |
| 9,138,279 B2 | 9/2015 | Laposta et al. |
| 9,149,307 B2 | 10/2015 | Sandstrom et al. |
| 9,216,044 B2 | 12/2015 | Nuckley et al. |
| 9,265,540 B2 | 2/2016 | Kirschman |
| 9,295,500 B2 | 3/2016 | Marigowda |
| 9,387,025 B2 | 7/2016 | Santangelo et al. |
| 9,446,507 B2 | 9/2016 | Nino et al. |
| 9,526,553 B2 | 12/2016 | Bess et al. |
| 9,572,605 B2 | 2/2017 | Shipp |
| 9,597,135 B1 | 3/2017 | Miller et al. |
| 9,642,654 B2 | 5/2017 | Reimels et al. |
| 9,649,139 B2 | 5/2017 | Sharifi-Mehr et al. |
| 9,687,285 B2 | 6/2017 | Robinson |
| 9,724,149 B2 | 8/2017 | Trieu et al. |
| 9,808,354 B2 | 11/2017 | Willis et al. |
| 9,820,740 B2 | 11/2017 | Zemlok et al. |
| 9,855,087 B2 | 1/2018 | Divincenzo et al. |
| 9,949,731 B2 | 4/2018 | Erramilli et al. |
| 9,968,384 B2 | 5/2018 | Fischer et al. |
| 9,987,066 B2 | 6/2018 | Stad et al. |
| 10,045,787 B2 | 8/2018 | Krebs et al. |
| 10,076,374 B2 | 9/2018 | Diduch et al. |
| 10,105,165 B2 | 10/2018 | Biedermann et al. |
| 10,117,684 B2 | 11/2018 | Saidha et al. |
| 10,160,105 B2 | 12/2018 | Nino et al. |
| 10,219,854 B2 | 3/2019 | Nino et al. |
| 10,274,021 B2 | 4/2019 | Victor et al. |
| 10,285,740 B2 | 5/2019 | May et al. |
| 10,349,986 B2 | 7/2019 | Wall et al. |
| 10,363,073 B2 | 7/2019 | Raina et al. |
| 10,390,967 B2 | 8/2019 | Livorsi et al. |
| 10,426,535 B2 | 10/2019 | Zander et al. |
| 10,433,883 B2 | 10/2019 | DiVincenzo et al. |
| 10,433,982 B2 | 10/2019 | Willis et al. |
| 10,448,978 B2 | 10/2019 | Wall et al. |
| 10,463,404 B2 | 11/2019 | Wall et al. |
| 10,470,805 B2 | 11/2019 | Biedermann et al. |
| 10,478,235 B2 | 11/2019 | Beale et al. |
| 10,568,668 B2 | 2/2020 | Biedermann et al. |
| 10,568,677 B2 | 2/2020 | DiVincenzo et al. |
| 10,582,925 B2 | 3/2020 | Marks et al. |
| 10,603,078 B2 | 3/2020 | Simpson et al. |
| 10,639,080 B2 | 5/2020 | Sharifi-Mehr et al. |
| 10,646,261 B2 | 5/2020 | Folger et al. |
| 10,653,457 B2 | 5/2020 | Erramilli et al. |
| 10,660,687 B2 | 5/2020 | Goodwin, Jr. et al. |
| 10,682,167 B2 | 6/2020 | Sandstrom et al. |
| 10,702,315 B2 | 7/2020 | Lindner |
| 10,702,316 B2 | 7/2020 | Heuer |
| 10,709,488 B2 | 7/2020 | Diduch et al. |
| 10,729,419 B2 | 8/2020 | Diduch et al. |
| 10,751,092 B2 | 8/2020 | Biedermann et al. |
| 10,765,466 B2 | 9/2020 | Stad et al. |
| 10,779,872 B2 | 9/2020 | Smith et al. |
| 10,869,751 B2 | 12/2020 | Diduch et al. |
| 10,874,448 B2 | 12/2020 | Rees et al. |
| 2002/0166421 A1 | 11/2002 | Bowerman |
| 2002/0169453 A1 | 11/2002 | Berger |
| 2006/0241600 A1 | 10/2006 | Ensign et al. |
| 2007/0010816 A1 | 1/2007 | Wilkinson et al. |
| 2007/0122764 A1 | 5/2007 | Balfour et al. |
| 2008/0041196 A1 | 2/2008 | Companioni et al. |
| 2008/0071274 A1 | 3/2008 | Ensign |
| 2008/0147128 A1 | 6/2008 | Fritzinger |
| 2008/0200918 A1 | 8/2008 | Spitler et al. |
| 2008/0215099 A1 | 9/2008 | Balfour et al. |
| 2008/0243190 A1* | 10/2008 | Dziedzic ........... A61B 17/7091 606/264 |
| 2008/0269768 A1 | 10/2008 | Schwager et al. |
| 2009/0005787 A1 | 1/2009 | Crall et al. |
| 2009/0264895 A1 | 10/2009 | Gasperut et al. |
| 2010/0249798 A1 | 9/2010 | Sournac et al. |
| 2010/0312279 A1* | 12/2010 | Gephart ........... A61B 17/00234 606/279 |
| 2011/0137320 A1 | 6/2011 | von Oepen |
| 2011/0160775 A1 | 6/2011 | Carls et al. |
| 2011/0270322 A1 | 11/2011 | Olsen et al. |
| 2011/0282398 A1 | 11/2011 | Overes et al. |
| 2011/0313463 A1* | 12/2011 | McLean ........... A61B 17/7085 606/279 |
| 2012/0203288 A1 | 8/2012 | Lange et al. |
| 2012/0239095 A1 | 9/2012 | Barrall |
| 2013/0072984 A1 | 3/2013 | Robinson |
| 2013/0072986 A1 | 3/2013 | Robinson |
| 2014/0018816 A1 | 1/2014 | Fenn et al. |
| 2014/0066945 A1 | 3/2014 | Humphreys et al. |
| 2014/0288567 A1 | 9/2014 | Kroll |
| 2014/0324062 A1 | 10/2014 | Heuer et al. |
| 2015/0201987 A1 | 7/2015 | Lemoine et al. |
| 2015/0250521 A1 | 9/2015 | Poker et al. |
| 2015/0374417 A1 | 12/2015 | Petit et al. |
| 2018/0070941 A1 | 3/2018 | Zemlok et al. |
| 2018/0146990 A1 | 5/2018 | Manzanares et al. |
| 2018/0235684 A1 | 8/2018 | Hawkes et al. |
| 2018/0353224 A1 | 12/2018 | Kam et al. |
| 2019/0175193 A1 | 6/2019 | Fenn et al. |
| 2019/0254729 A1 | 8/2019 | Rohlfing et al. |
| 2019/0254730 A1 | 8/2019 | Rohlfing et al. |
| 2019/0329388 A1 | 10/2019 | Erickson et al. |
| 2019/0336187 A1 | 11/2019 | Zander et al. |
| 2019/0357948 A1 | 11/2019 | Wall et al. |
| 2019/0374263 A1 | 12/2019 | Wall et al. |
| 2020/0030015 A1 | 1/2020 | Grizzard et al. |
| 2020/0038064 A1 | 2/2020 | Stoklund et al. |
| 2020/0078056 A1 | 3/2020 | Biedermann et al. |
| 2020/0100817 A1 | 4/2020 | DiVincenzo et al. |
| 2020/0100824 A1 | 4/2020 | DiVincenzo et al. |
| 2020/0113603 A1 | 4/2020 | Simpson et al. |
| 2020/0121397 A1 | 4/2020 | Elliott et al. |
| 2020/0121398 A1 | 4/2020 | Elliott et al. |
| 2020/0205805 A1 | 7/2020 | Marks et al. |
| 2020/0229849 A1 | 7/2020 | Biedermann et al. |
| 2020/0237412 A1 | 7/2020 | Erramilli et al. |

(56) References Cited

U.S. PATENT DOCUMENTS

2020/0340558 A1   10/2020   Riemhofer et al.
2020/0375638 A1   12/2020   Avidano et al.
2020/0390478 A1   12/2020   Rodriguez et al.
2020/0390486 A1   12/2020   Rodriguez et al.

\* cited by examiner

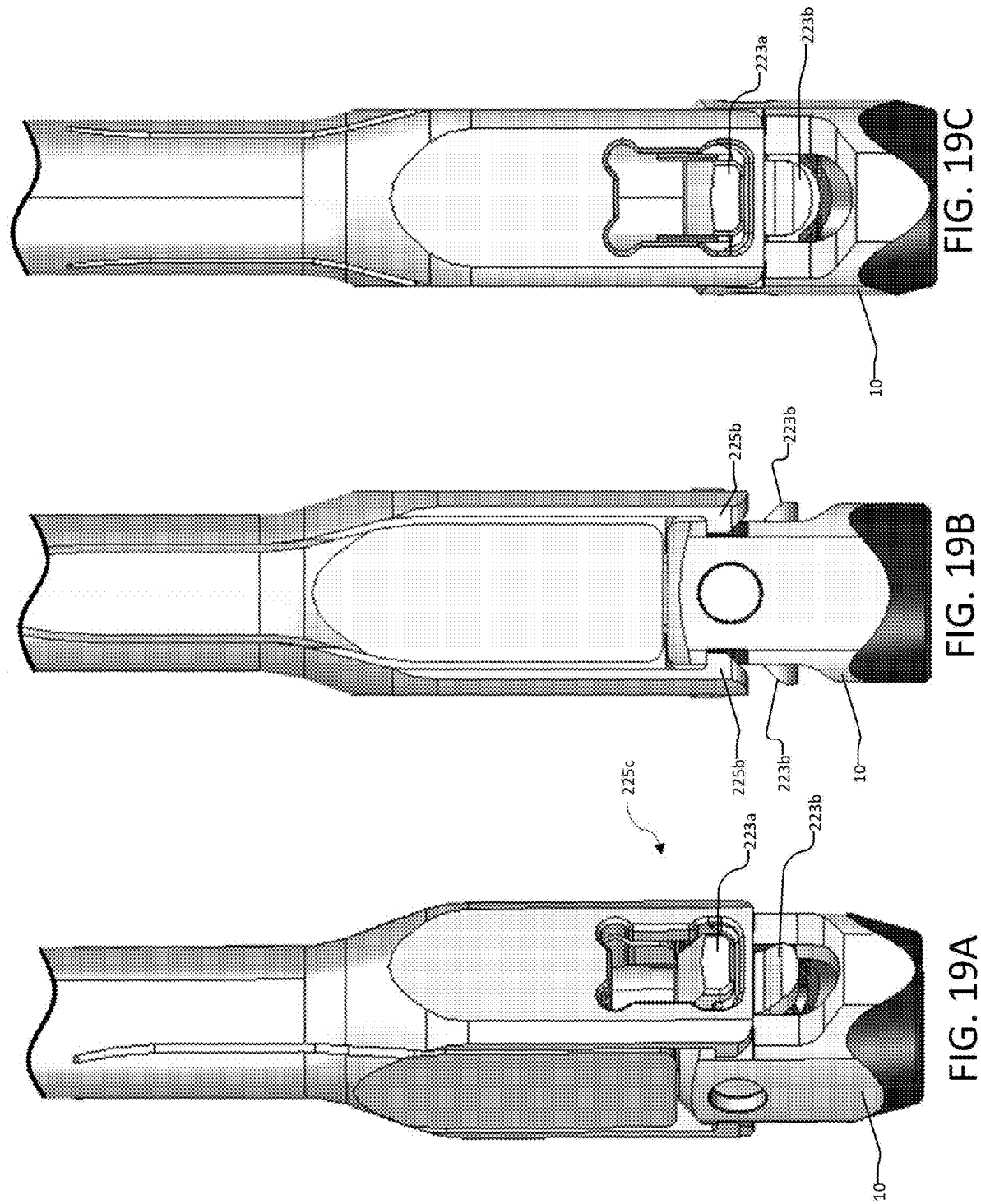

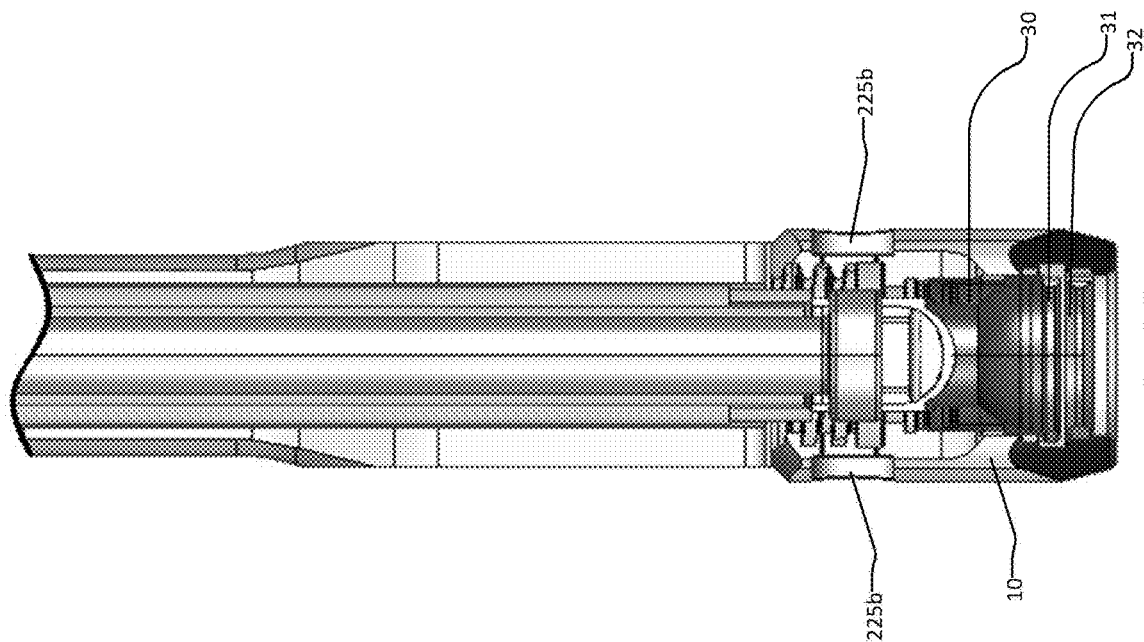
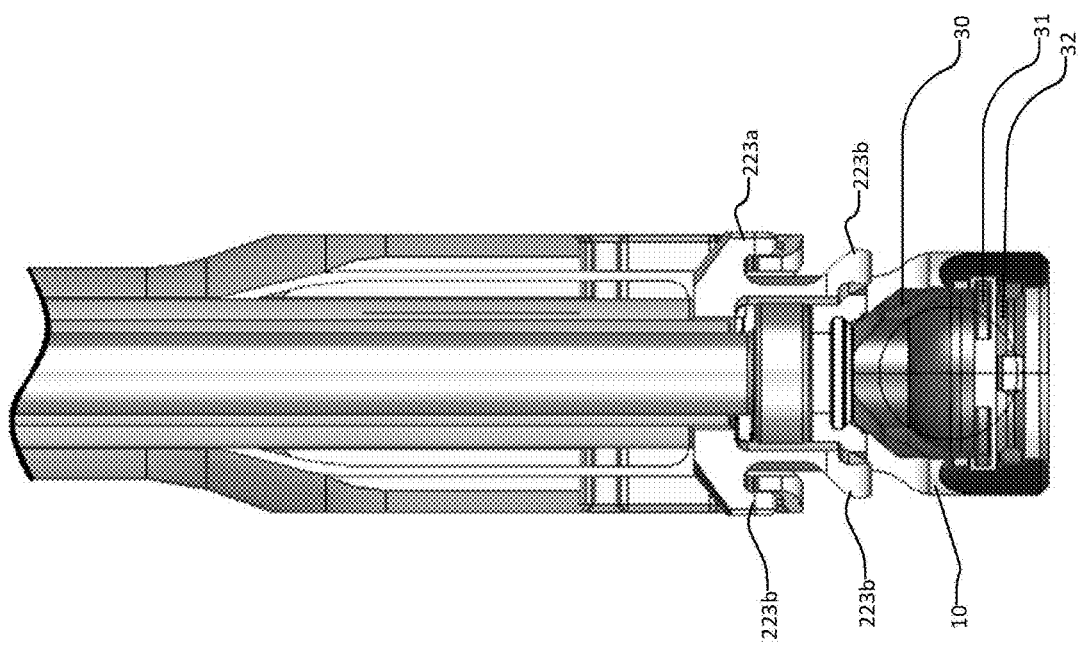

INSTRUMENT FOR LOCKING ORTHOPEDIC SCREWS

CROSS-REFERENCE TO RELATED APPLICATIONS

This application is a continuation in part of and claims priority to U.S. patent application Ser. No. 16/830,377, titled Powered Modular Head Locker, filed Mar. 26, 2020, the disclosure of which is hereby incorporated in its entirety. Additionally, this application incorporates the disclosure of co-related patent application, U.S. patent application Ser. No. 16/405,636, titled Head Assembly Inserters, filed May 7, 2019 in its entirety.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation, and exercise can be effective, however, may fail to relieve the symptoms associated with these disorders. Surgical treatment of these spinal disorders includes correction, fusion, fixation, discectomy, laminectomy, and/or implantable prosthetics. As part of these surgical treatments, spinal constructs, which include implants such as bone fasteners, connectors, plates, and vertebral rods are often used to provide stability to a treated region. These implants can redirect stresses away from a damaged or defective region while healing takes place to restore proper alignment and generally support the vertebral members. Surgical instruments are employed, for example, to engage the fasteners for attachment to two or more vertebral members. This disclosure describes improvements over these prior technologies.

SUMMARY

The present disclosure relates to surgical instruments, surgical systems, and associated methods for operating the surgical instrument and the surgical systems.

In one aspect, the disclosure provides for a surgical instrument. The surgical instrument may include a drive shaft that is axially aligned with a central axis of the surgical instrument, for example. The drive shaft may include a first mating end and be rotatably supported within a drive housing supporting the first mating end, for example. The surgical instrument may further include an outer shaft including an outer receiver interface configured to selectively couple and uncouple to a connecting portion of a receiver, and a plunger, for example. The plunger may be axially aligned with the central axis of the surgical instrument and include a second mating end that is disposed within the drive housing, for example. In various embodiments, the second mating end may be axially aligned with and in contact with the first mating end, for example. In various embodiments, the plunger may be configured to linearly translate forward and backward along the central axis upon rotation of the drive shaft around the central axis, for example.

In another aspect, the outer shaft may include at least one flexible arm that is configured to bow laterally outward with respect to the central axis to facilitate selectively coupling and uncoupling with the connecting portion of the receiver, for example.

In another aspect, an inner shaft may be disposed within the outer shaft, at least partly, for example. In various embodiments, the inner shaft may include an inner receiver interface that is configured to selectively couple and uncouple from the outer receiver interface, for example. Additionally, in various embodiments, when the inner receiver interface is coupled with the outer receiver interface the outer receiver interface may be prevented from bowing laterally outward with respect to the central axis, for example.

In another aspect, a distal end of the outer shaft may include a first flexible arm and a second flexible arm disposed opposite the first flexible arm, for example. The first flexible arm may include a first platform and the second flexible arm may include a second platform, for example. In various embodiments, the first flexible arm and the second flexible arm may define a recess between the first flexible arm and the second flexible arm. In various embodiments, the first flexible arm and the second flexible arm may each be configured to bow laterally outward with respect to the central axis to thereby widen the recess and facilitate selectively coupling and uncoupling with the connecting portion of the receiver, for example. In various embodiments, the connecting portion of the receiver may include a first detent and a second detent, and the first platform and the second platform may be configured to mate with the first detent and the second detent, respectively.

In another aspect, an inner shaft may be disposed at least in part within an outer shaft and a distal end of the inner shaft may include an inner receiver interface including a first hook and a second hook, for example. In various embodiments, the first hook may be configured to couple to the first flexible arm and the second hook being configured to couple to the second flexible arm, and when the first hook is coupled to the first flexible arm and the second hook is coupled to the second flexible arm, the first flexible arm and the second flexible arm may be prevented from bowing laterally outward with respect to the central axis, for example.

In another aspect, a tip of the inner receiver interface may include a first sloped surface and a second sloped surface, and the first sloped surface and the second sloped surface may each extend away from and being angled with respect to the central axis. Additionally, the outer shaft may be movable forward and backward along the central axis with respect to the inner shaft, for example. In various embodiments, the outer shaft is configured to slide forward along the central axis such that the first flexible arm contacts the first sloped surface and the second flexible arm contacts the second sloped surface thereby causing the first flexible arm and the second flexible arm to bow outward with respect to the central axis, for example.

In another aspect, a biasing member may be configured to urge the second mating end of the plunger into contact with the first mating end of the drive shaft, for example.

In another aspect, the drive housing includes a contoured interior supporting the first mating end, and the second mating end may be disposed within the contoured interior, for example. In various embodiments, the contoured interior may include a plurality of grooves extending in a direction parallel with the central axis, the first mating end may include a first plurality of ramps having a first plurality of peaks and a first plurality of valleys, and the second mating end may include a second plurality of ramps having a second plurality of peaks and a second plurality of valleys, for example. In various embodiments, the first mating end may further include a positioning ball extending laterally from a side surface of the first mating end in a direction perpendicular to the central axis, and the positioning ball may be selectively seated within one groove of the plurality of grooves, for example. Additionally, the positioning ball may be configured to align the first plurality of ramps with the second plurality of ramps such that the first plurality of peaks may be aligned with the second plurality of valleys and the first plurality of valleys may be aligned with the second plurality of peaks.

In another aspect, a method for operating a surgical instrument, is disclosed. The method may include receiving at least a portion of a receiver in a corresponding receiver interface of a surgical instrument, and rotating a drive shaft having a first mating end against a second mating end of a plunger, for example. The method may also include linearly translating the plunger in a first direction towards the receiver, applying a pushing force on the receiver via the plunger, and biasing the plunger in a second direction towards the drive shaft, for example.

In another aspect, the method may further include bending at least one flexible arm of the corresponding receiver interface laterally outward with respect to a central axis of the surgical instrument such that the at least one flexible arm surrounds the receiver, at least partly, for example.

In another aspect, the method may further include mating an inwardly extending platform of the at least one flexible arm within a connecting portion of the receiver, for example. In various embodiments, the connecting portion may have a size and shape generally corresponding to the inwardly extending platform, for example.

In another aspect, the method may further include securing the at least one flexible arm with a hook portion of an inner shaft thereby preventing the at least one flexible arm from bending laterally outward, for example.

In another aspect, the method may further include securing the at least one flexible arm to the receiver after the mating the inwardly extending platform step, for example.

In another aspect, the method may further include biasing the mating end of the plunger against the mating end of the rotatable drive shaft, for example.

In another aspect, the method may further include biasing the drive shaft such that the mating end of the drive shaft may be properly aligned with the mating end of the plunger, for example.

In another aspect, the method may further include uncoupling the receiver from the surgical instrument by pushing down on an outer shaft of the surgical instrument such that the at least one flexible arm contacts a sloped surface of an inner shaft of the surgical instrument, for example. Additionally, the sloped surface may urge the at least one flexible arm outward and away from the receiver, for example.

In another aspect, the method may further include seating a positioning ball within a groove of a plurality of grooves having a size and shape generally corresponding to the positioning ball, and biasing the drive shaft into alignment with the plunger such that peaks of the mating end of the drive shaft are aligned with valleys of the mating end of the plunger.

In another aspect, the linearly translating the plunger in a first direction step may be facilitated by a positioning ball and grooves having a shape and size generally corresponding to the positioning ball, for example. Additionally, the positioning ball may be configured to continuously bias the drive shaft into alignment with the plunger such that peaks of the mating end of the rotatable shaft are aligned with valleys of the mating end of the plunger, for example.

In another aspect, a modular surgical instrument for fixing a receiver to a bone screw is disclosed. The instrument may include a first component configured to selectively couple and uncouple with a second component, and the first component and second component may define a central axis of the surgical instrument having a distal end and a proximal end, for example. In various embodiments, the first component may include a drive shaft axially aligned with the central axis of the surgical instrument, and the drive shaft may include a first mating end and may be rotatably supported within a drive housing, for example. In various embodiments, the drive housing may include a contoured interior supporting the first mating end, for example. Additionally, the second component may include an outer shaft including an outer receiver interface disposed at the distal end, the outer receiver interface having a first flexible arm and a second flexible arm defining a recess configured to receive a receiver, for example. In various embodiments, the first flexible arm and second flexible arm may be configured to selectively couple and uncouple to a connecting portion of a receiver by bowing laterally outward with respect to the central axis and enlarging the recess, for example. Additionally, in various embodiments, an inner shaft may be disposed within the outer shaft, at least partly, and the inner shaft may include an inner receiver interface disposed at the distal end and having a first hook and a second hook, for example. Additionally, the first hook may be configured to couple to the first flexible arm in a locked position and the second hook may be configured to couple to the second flexible arm in a locked position, for example. In various embodiments, a plunger may be axially aligned with the central axis of the surgical instrument and include a second mating end disposed within the countered interior of the drive housing, for example. Additionally, the second mating end may be aligned with and in contact with the first mating end, for example. In various embodiments, the plunger may be configured to linearly translate forward and backward along the central axis upon rotation of the drive shaft around the central axis, for example.

In another aspect, a biasing member configured to urge the second mating end of the plunger into contact with the first mating end of the drive shaft may be provided. Additionally, in various embodiments, the first mating end may include a first plurality of ramps having a first plurality of peaks and a first plurality of valleys and the second mating end may include a second plurality of ramps having a first plurality of peaks and a second plurality of valleys. Furthermore, in various embodiments, the contoured interior may include a plurality of grooves extending in a direction parallel with the central axis, for example. Further still, in various embodiments, the first mating end may include a positioning ball extending laterally from a side surface of the first mating end in a direction perpendicular to the central axis, and the positioning ball may have a size and shape generally corresponding to the plurality of grooves, for example. Additionally, the positioning ball may be selectively seated within one groove of the plurality of grooves and may be configured to align the first plurality of peaks with the second plurality of valleys and the first plurality of valleys with the second plurality of peaks, for example.

The foregoing and other objects, features and advantages of the invention will be apparent from the following more particular descriptions of exemplary embodiments of the invention as illustrated in the accompanying drawings wherein like reference numbers generally represent like parts of the disclosure.

BRIEF DESCRIPTION OF DRAWINGS

The following drawings are illustrative of particular embodiments of the present disclosure and therefore do not limit the scope of the present disclosure. The drawings are not to scale and are intended for use in conjunction with the explanations in the following detailed description.

FIG. 19A is an off-angle side view of the distal tip of the second component coupled to a receiver.

FIG. 19B is straight side view of the distal tip of the second component coupled to a receiver from a first side.

FIG. 19C is straight side view of the distal tip of the second component coupled to a receiver from a second side.

FIG. 20A is a cross section view of the distal tip of the second component coupled to a receiver of FIG. 19B.

FIG. 20B is a cross section view of the distal tip of the second component coupled to a receiver of FIG. 19C.

DETAILED DESCRIPTION

Figure 1:
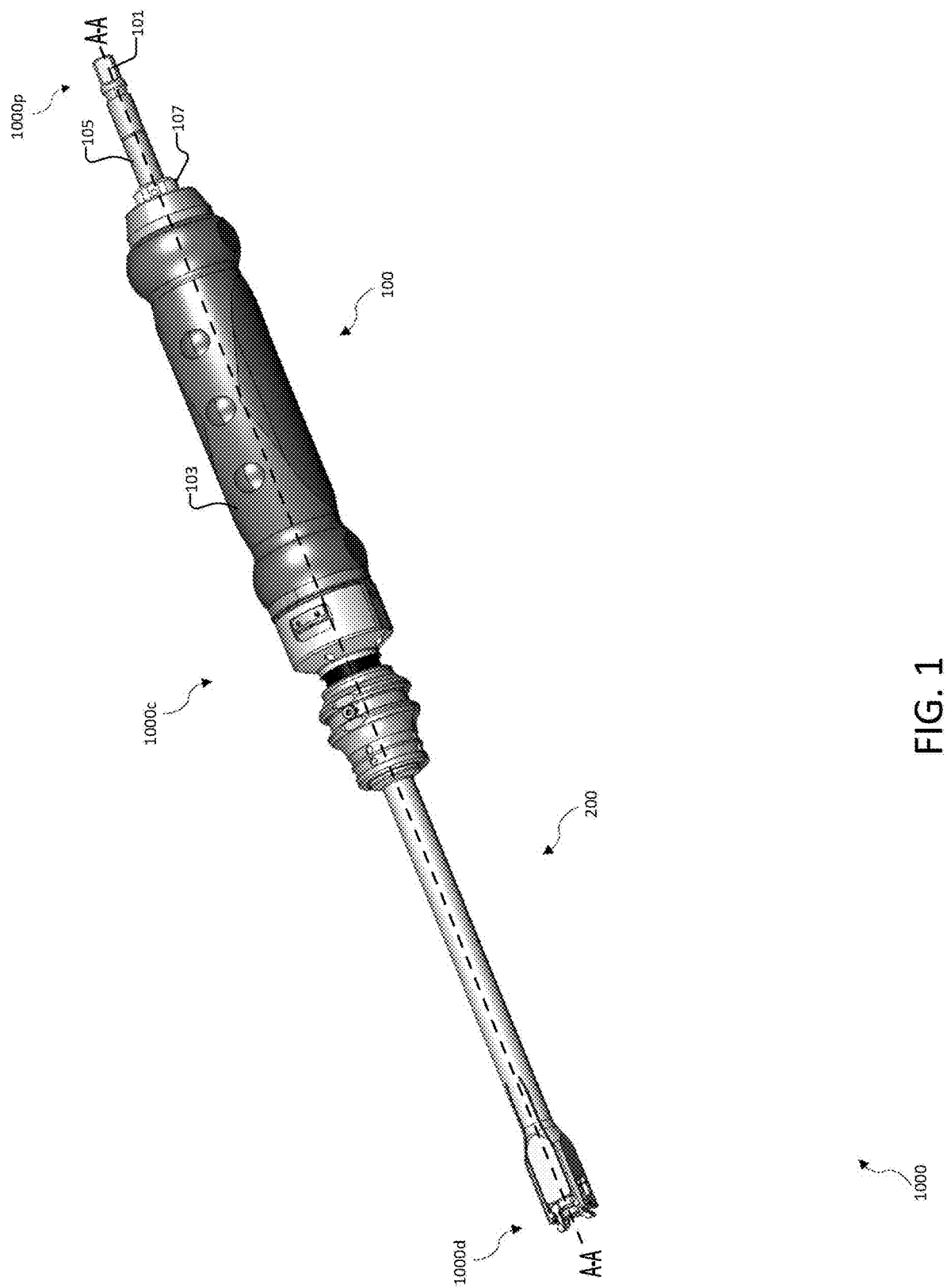
FIG. 1 is an example perspective view of an assembled modular surgical instrument.

The following discussion omits or only briefly describes certain conventional features related to surgical systems for treating the spine, which are apparent to those skilled in the art. It is noted that various embodiments are described in detail with reference to the drawings, in which like reference numerals represent like parts and assemblies throughout the several views. Reference to various embodiments does not limit the scope of the claims appended hereto. Additionally, any examples set forth in this specification are intended to be non-limiting and merely set forth some of the many possible embodiments for the appended claims. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

Embodiments of the present disclosure relate generally, for example, to medical devices and methods for treating musculoskeletal disorders, and more particularly, to surgical systems and methods for treating the spine. Embodiments of the devices, methods, and systems are described below with reference to the Figures.

Figure 13:
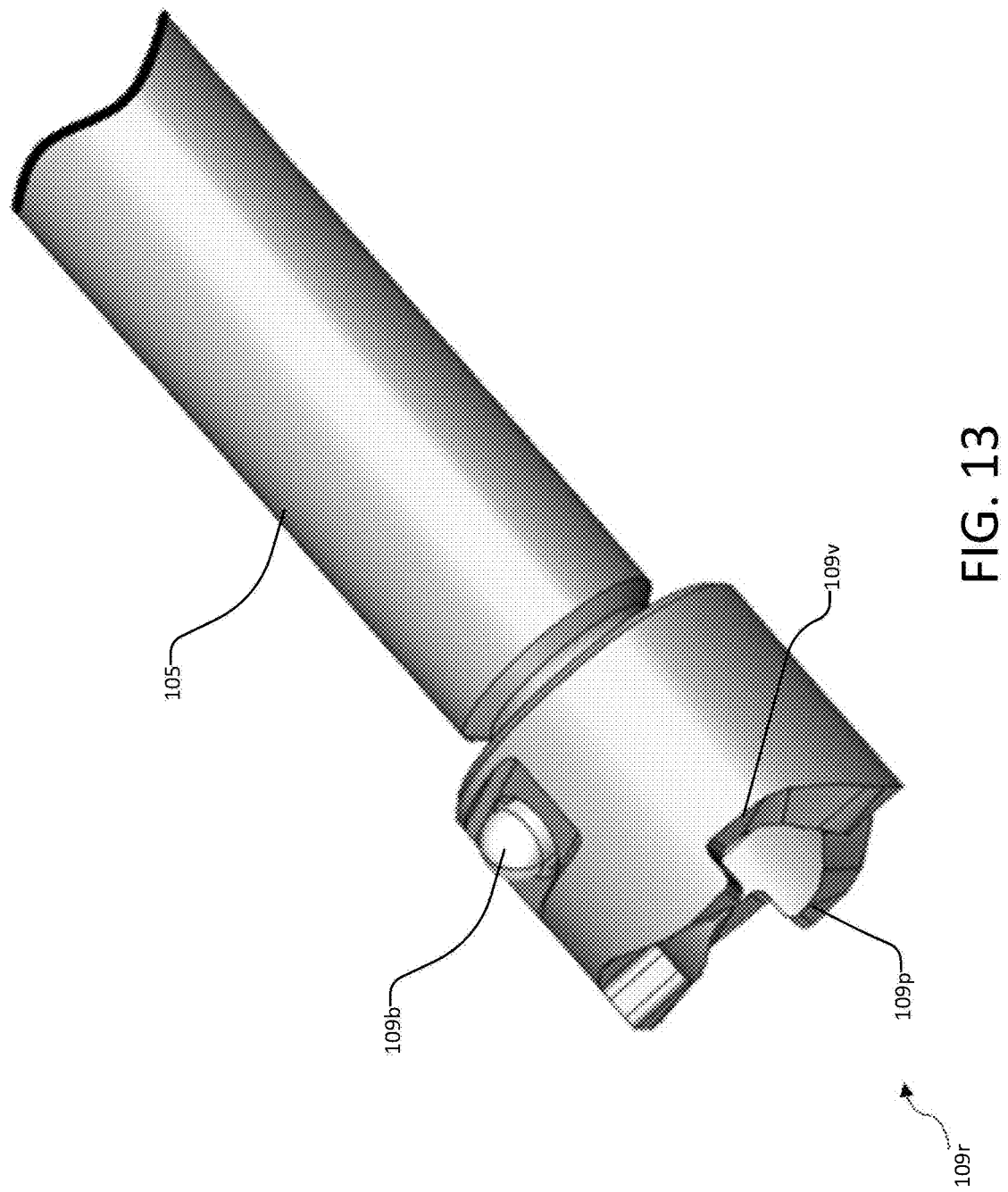
FIG. 13 is a perspective view of a rotatable drive shaft of the first component.
Figure 14:
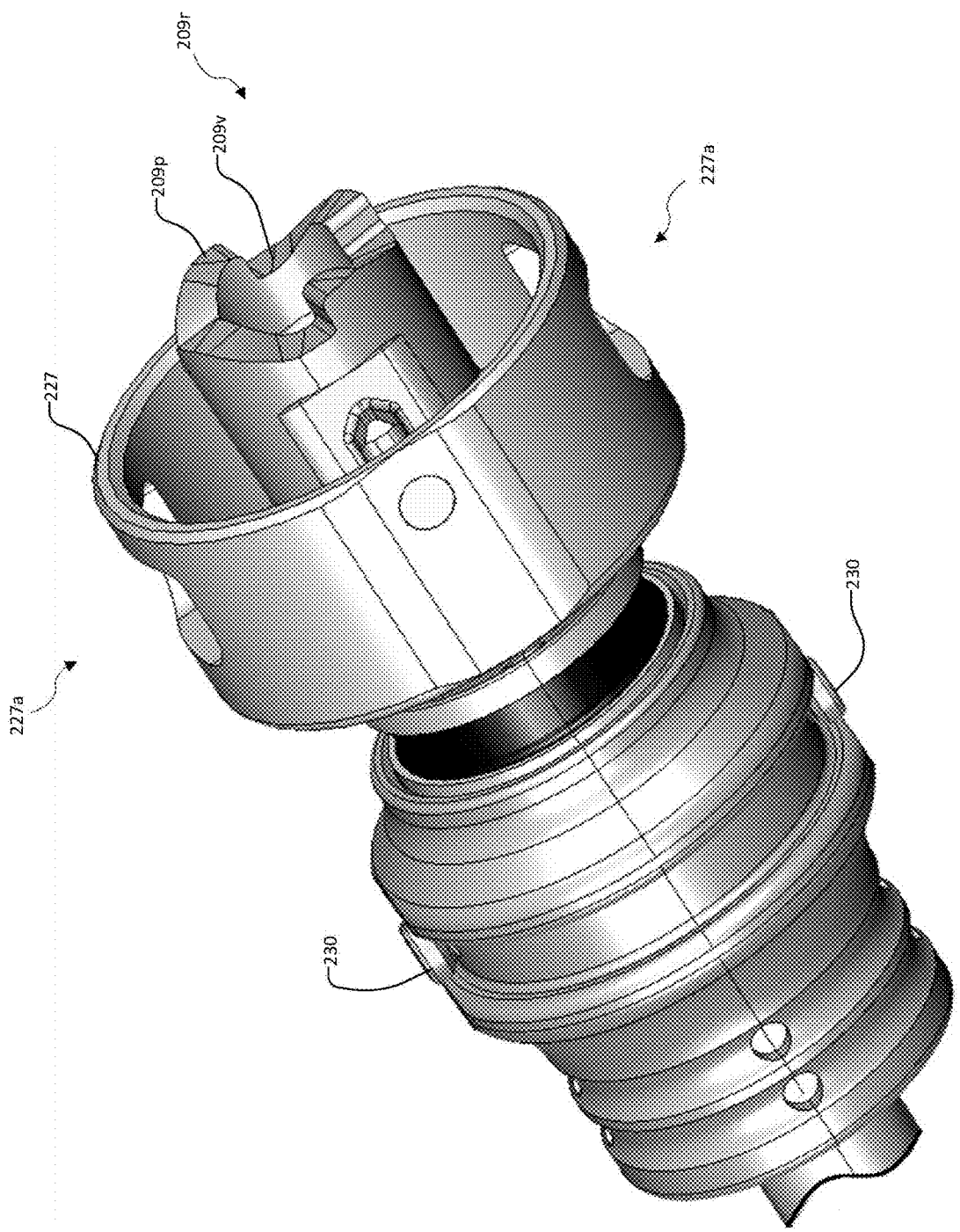
FIG. 14 is a perspective view of a plunger of the second component.

FIG. 1 is an example perspective view of a surgical instrument 1000. Surgical instrument 1000 may also be referred to as a "head locker" in the industry or also as an instrument for locking polyaxial orthopedic screws, for example. The surgical instrument 1000 may be a modular instrument formed primarily of a first component 100 and a second component 200, for example. In various embodiments, the first component 100 and the second component 200 may be able to selectively couple and uncouple from one another via a coupling portion 1000c, for example. Surgical instrument 1000 may include a proximal end 1000p and a distal end 1000d. The distal end may be configured for connecting to a receiver 10 and/or head assembly 1 (see FIG. 2), for example. The proximal end may be defined by a rotatable drive end 101 for coupling with a rotational part of an external instrument or tool, for example. An illustrative external power instrument is shown in FIGS. 13-14 of U.S. patent application Ser. No. 16/830,377, titled Powered Modular Head Locker, the disclosure of which is incorporated herein in its entirety. The external power instrument can include, but is not limited to, a high-speed surgical drill that has a part number 66320805 and is available from Medtronic of Minneapolis, Minnesota.

The rotatable drive end 101 defines an end of a rotatable drive shaft 105 that extends longitudinally along a central axis A-A of the surgical instrument 1000 in a direction towards the proximal end 1000p of the surgical instrument, for example. The drive end 101 may be sized and shaped to be received in a socket of the external power instrument's rotational part. Alternatively, in other embodiments the drive end 101 may be coupled to a manual hand driver (not illustrated). The rotatable drive end 101 and rotatable drive shaft 105 are designed such that the external power instrument is able to cause rotation of the drive shaft 105 in a clockwise direction and/or a counter clockwise direction. In the scenario shown in FIG. 1, the drive end has a square shape, for example. The present solution is not limited in this regard since the drive end 101 can have other shapes selected in accordance with a given application (e.g., a cross shape, a star shape or any other shape that allows the transfer of torque to the rotatable drive shaft 105). Notably, the drive shaft 105 may freely rotate within the interior of the first component 100 without causing rotation of the handle 103, for example.

Figure 2:
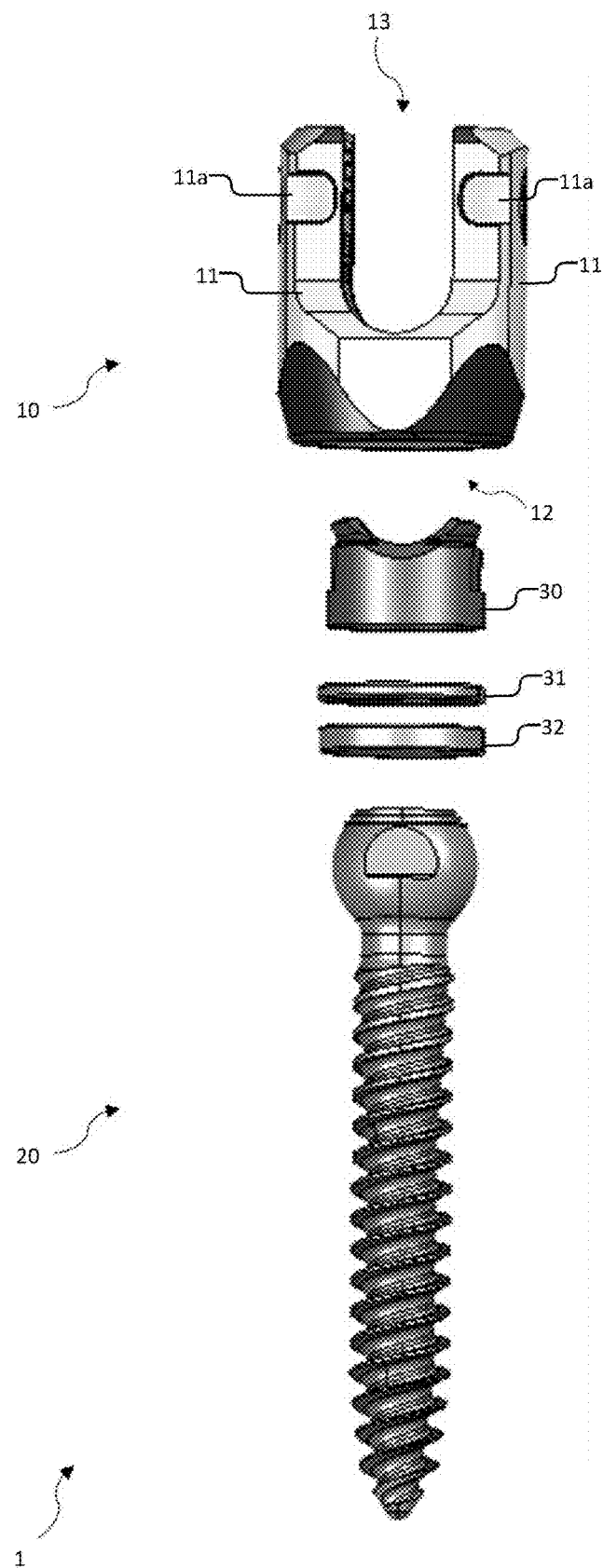
FIG. 2 is an example front view of a head assembly.

FIG. 2 is an example front view of a head assembly 1. The head assembly 1 may include a receiver 10 that houses a crown 30, an upper retainer 31, and a lower retainer 32 within a base portion 12 of the receiver 10, for example. The receiver base portion 12 may include a receiving portion that defines a cavity within the receiver base portion 12. The receiving portion may include an upper chamber, an expansion chamber, and a lower chamber, for example and as described in detail in U.S. patent application Ser. No. 16/405,636, titled Head Assembly Inserters, the disclosure of which is incorporated herein by reference in its entirety. In various embodiments, receiver 10 may include a pair of arms 11 defining a top chamber 13 between the pair of arms 11. Each arm 11 may include an outside surface and an inside curved surface having a thread pattern configured to mate or mesh with a corresponding thread pattern of a set screw (not illustrated). Each arm 11 may include a pair of opposing lateral side walls that each have a substantially planar surface and a connecting portion 11a that is indented with respect to the planar surface, for example. Each connecting portion 11a may be an indented chamfered portion, an indented square portion, or the like, for example. Connecting portion 11a may be configured for connecting to surgical instrument 1000, as explained in further detail below.

Figure 3:
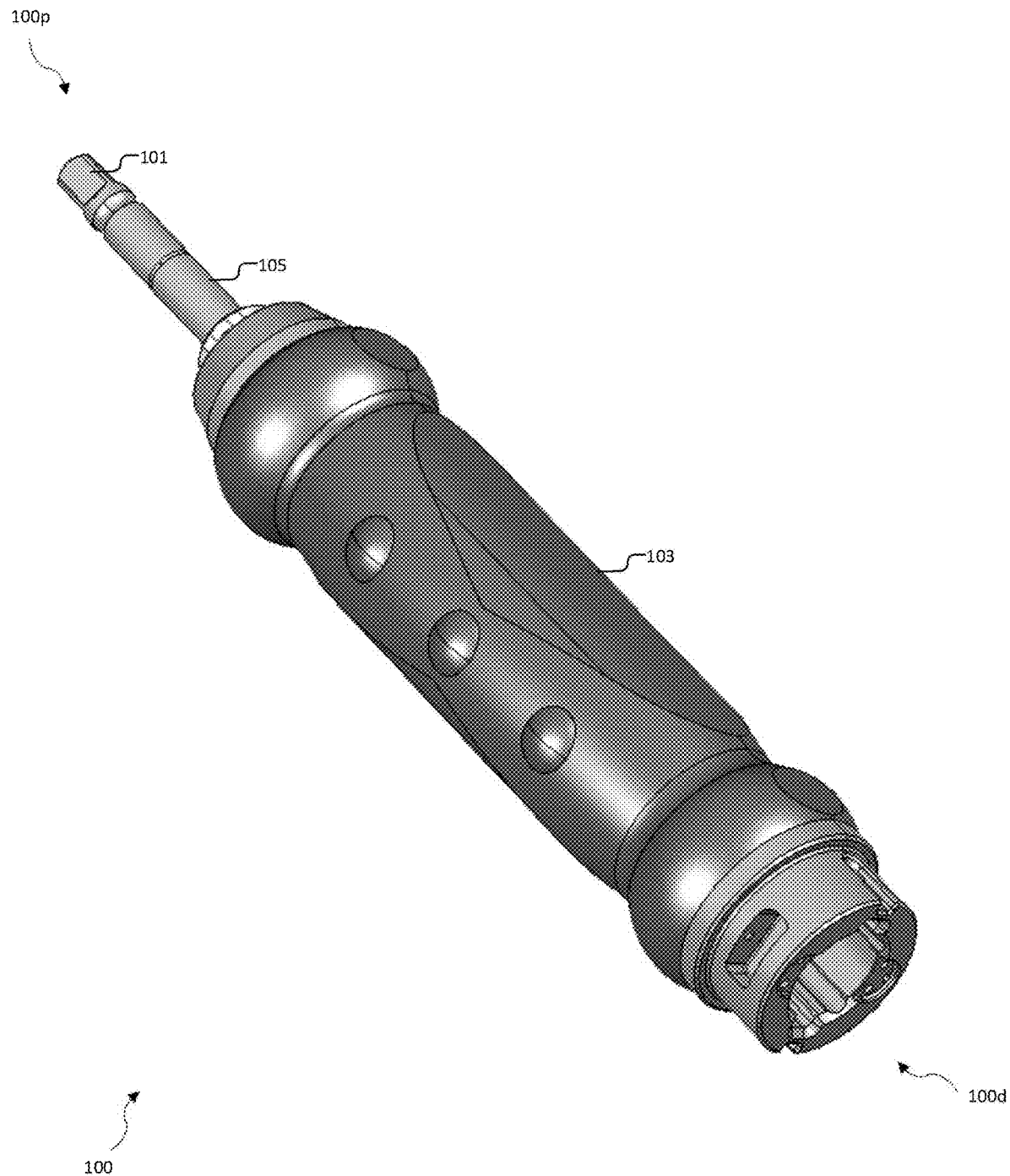
FIG. 3 is an example perspective view of a first component of the modular surgical instrument.
Figure 4:
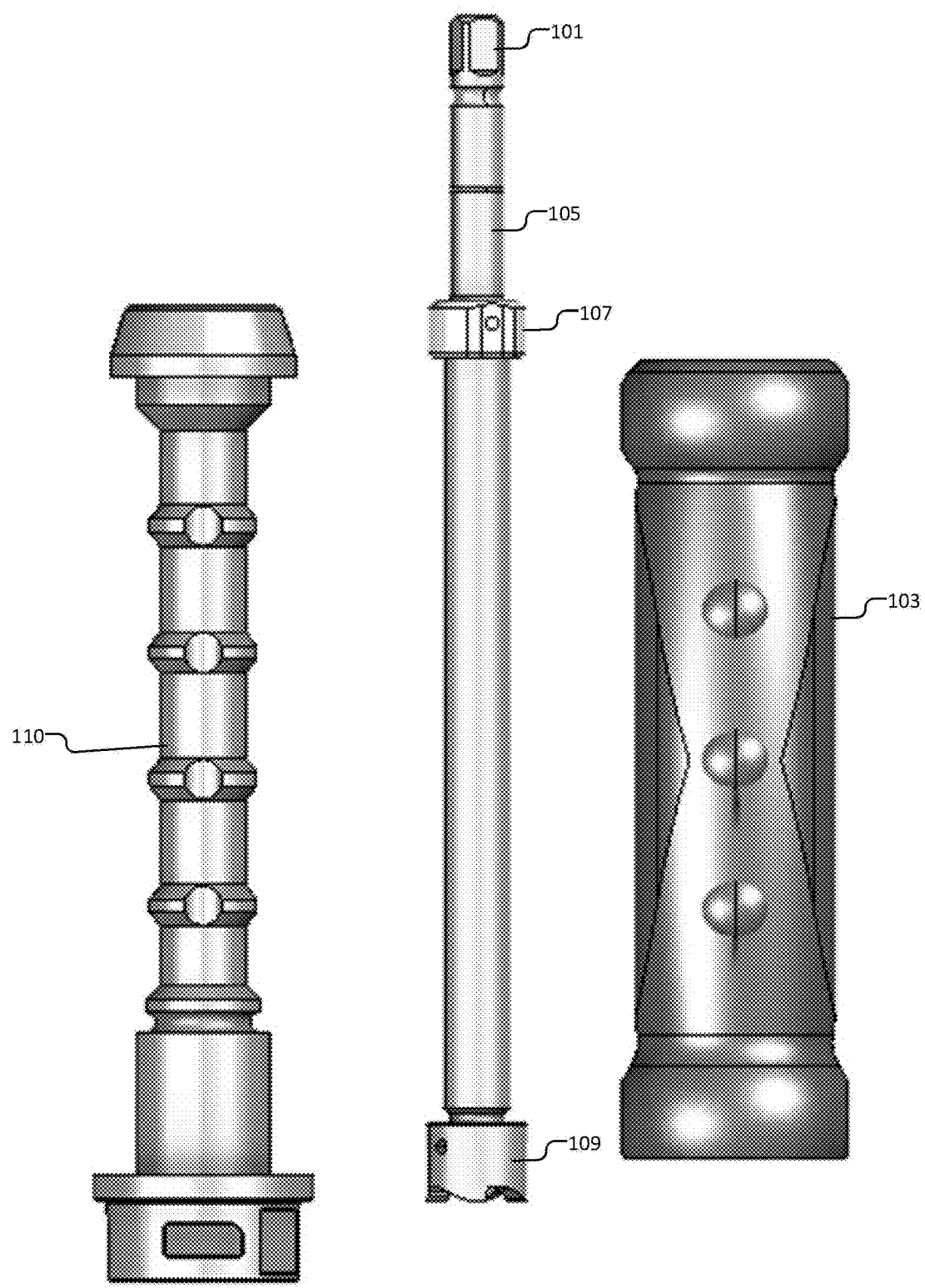
FIG. 4 is an example exploded parts view of the first component of FIG. 3.
Figure 5A:
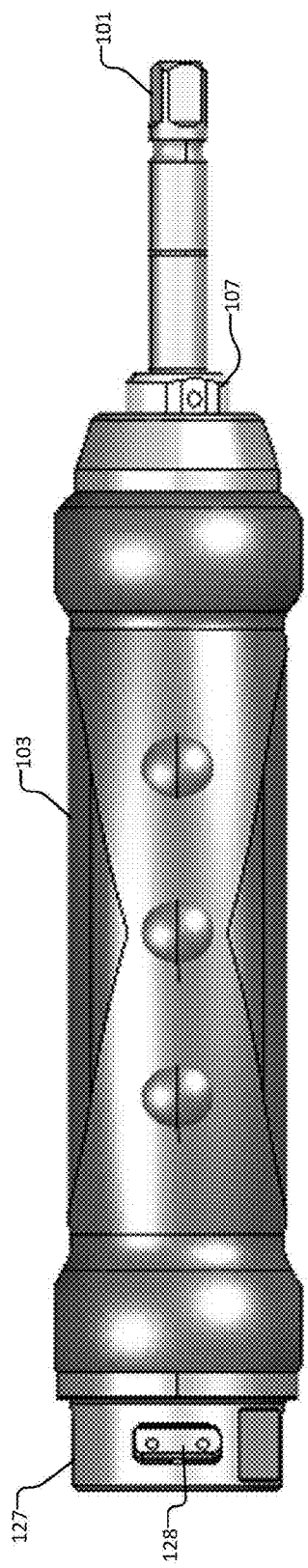
FIG. 5A is an example side view of the first component of FIG. 3.
Figure 5B:
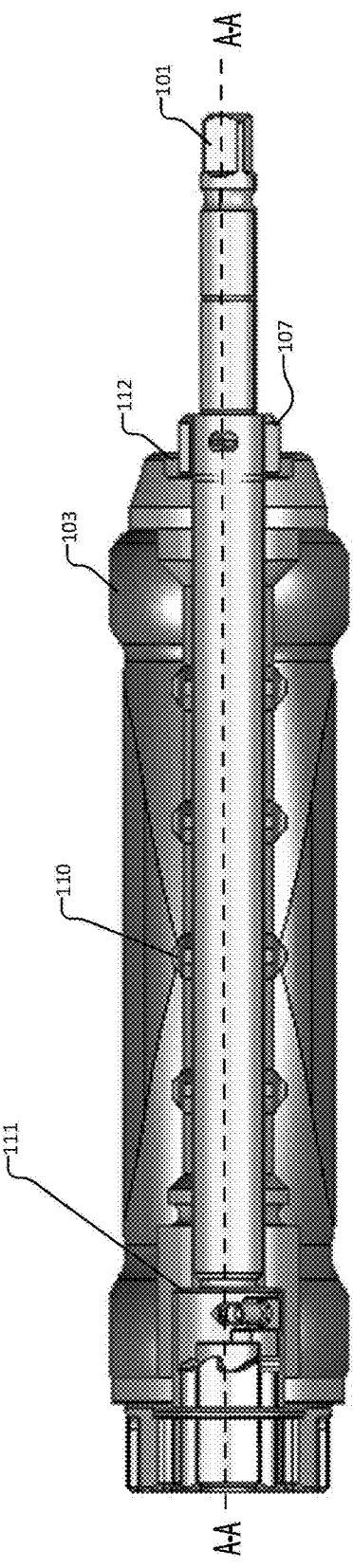
FIG. 5B is an example cross section view of the first component of FIG. 5A.

Referring generally to FIGS. 3-5B various example views of a first component 100 of the surgical instrument 1000 are shown. FIG. 3 is an example perspective view of the first component 100, and FIG. 4 is an example exploded parts view of the first component 100 of FIG. 3. FIG. 5A is an example side view of the first component 100 of FIG. 3 and FIG. 5B is an example cross section view of the first component 100 of FIG. 5A. First component 100 may have a proximal end 100p and a distal end 100d, for example. First component 100 may include a handle 103 for gripping the surgical instrument. Handle 103 may surround a drive housing 110 which in turn supports rotatable drive shaft 105 therein. Rotatable drive shaft 105 may freely rotate within drive housing 110 along axis A-A, for example. Rotatable drive shaft 105 may include a first mating end 109. First mating end 109 may generally have a greater cross sectional width than drive shaft 105, for example.

The rotatable drive shaft 105 may be disposed within the drive housing 110 such that it can rotate therein in clockwise and/or counter clockwise direction(s), but is unable to move linearly along the central axis A-A. For example, a retaining coupler 107, retaining interface 111, and/or receiving portion 112 may prevent the rotatable drive shaft 105 from moving linearly along central axis A-A. In this regard the rotatable drive shaft 105 may have a cross sectional width that is greater than a cross section width of the drive housing 110 at the retaining interface 111. Retaining interface 111 may include flange or the like that may engage an inner surface of drive housing 110, whereby the rotatable drive shaft 105 is prevented by the drive housing 110 from traveling linearly forward and/or backward along central axis A-A. The rotatable drive shaft 105 is also prevented from traveling linearly forward and/or backward along central axis A-A by, for example, a retaining coupler 107. Retaining coupler 107 may include, for example, a protrusion or pin securing it to rotatable drive shaft 105. In some embodiments, retainer coupler 107 may comprise a pressure fit ring, a friction fitting, an adhesive such as epoxy, and/or a seam such as a tac weld or the like. Retaining coupler 107 may also be seated within a receiving portion 112 of the drive housing 110 and have a cross sectional width greater than drive shaft 105. In various embodiments, receiving portion 112 may comprise a circumferential groove formed in an exterior surface of the drive housing 110. In this way, rotatable drive shaft 105 may be prevented from travelling linearly along axis A-A towards a proximal end 100p (forward) of first component 100 and may also be prevented from travelling linearly along axis A-A towards a distal end 100d (backward) of first component 100.

Figure 6:
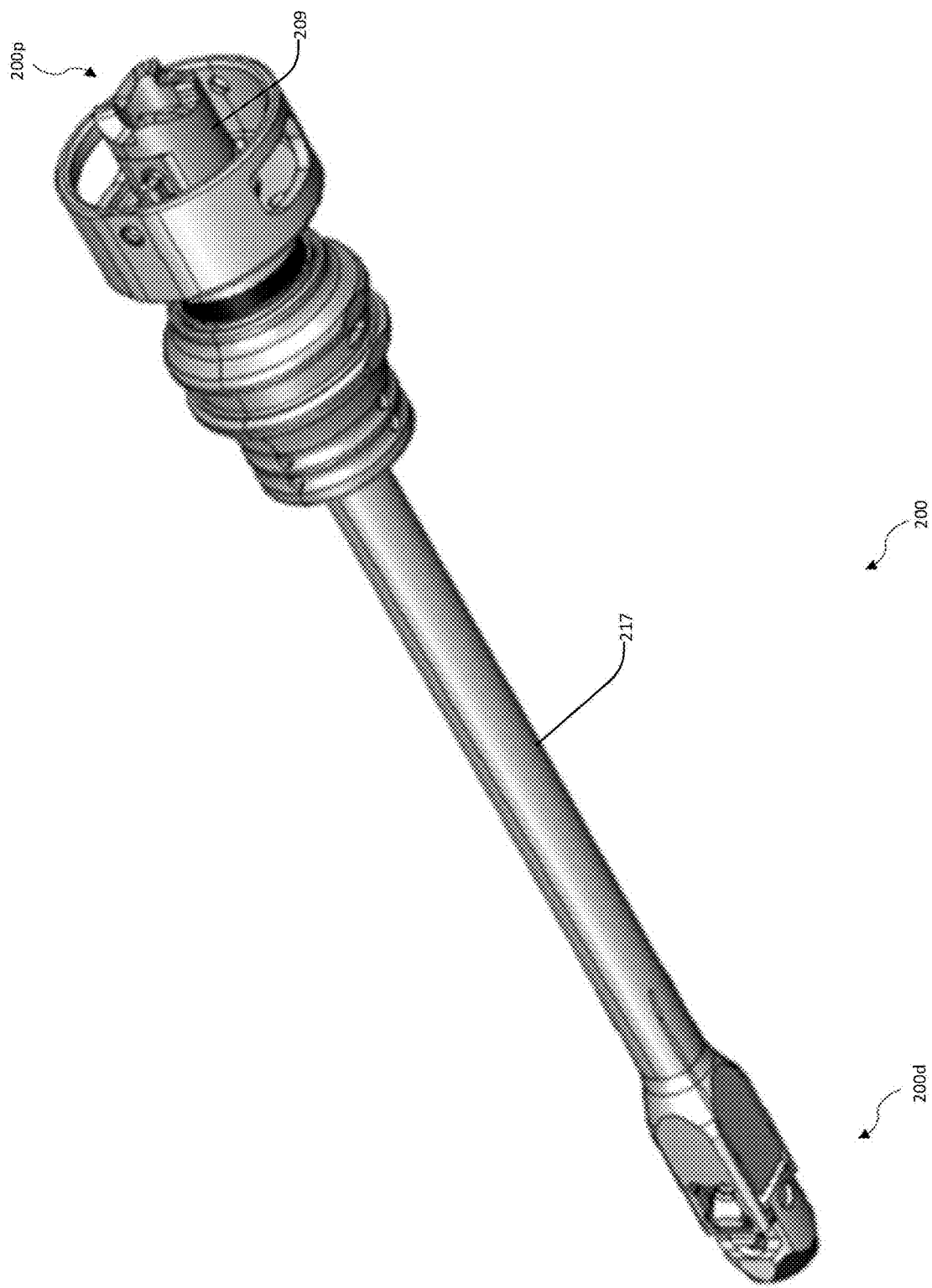
FIG. 6 is an example perspective view of a second component of the modular surgical instrument.
Figure 7:
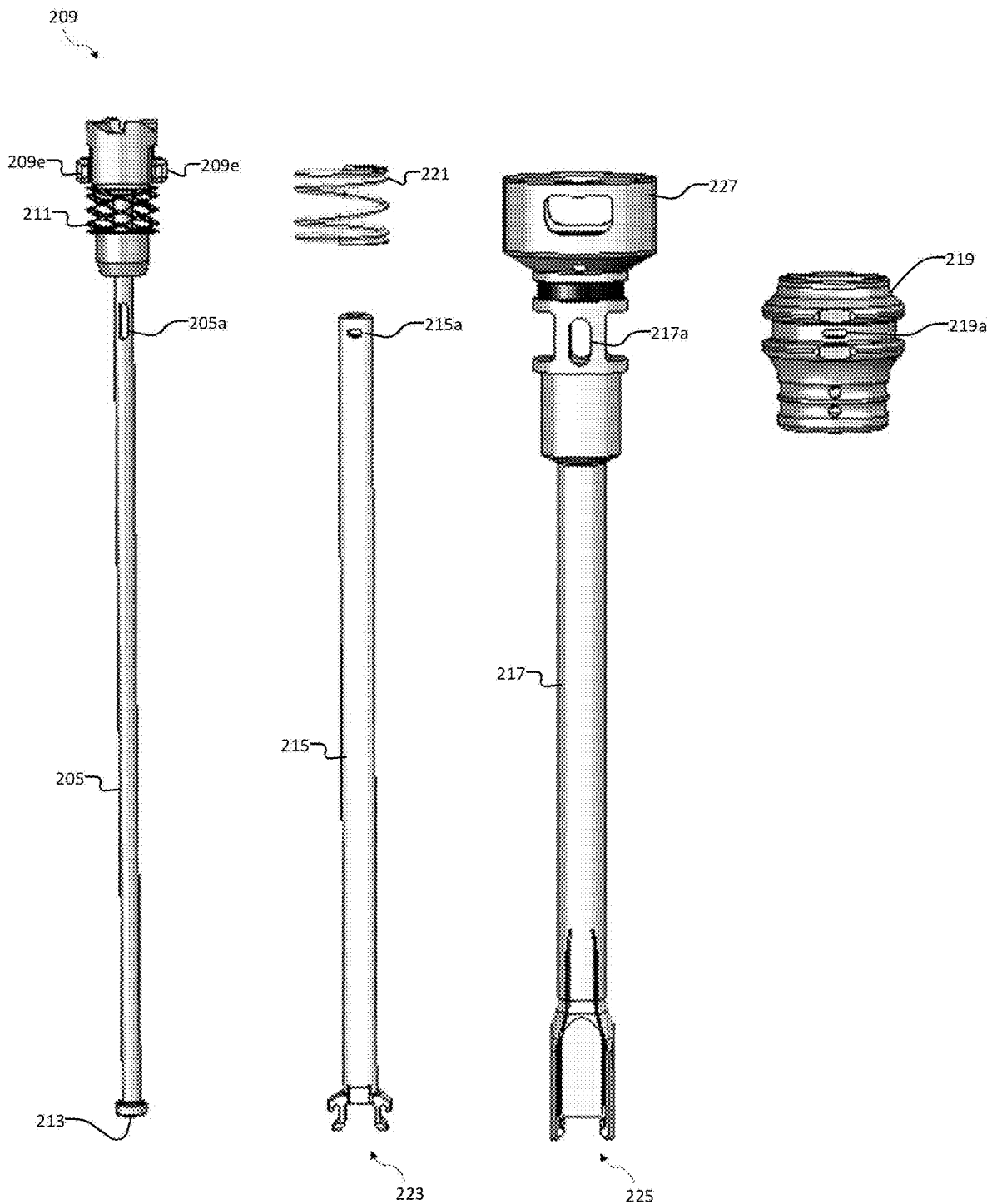
FIG. 7 is an example exploded parts view of the second component of FIG. 6.
Figure 8A:
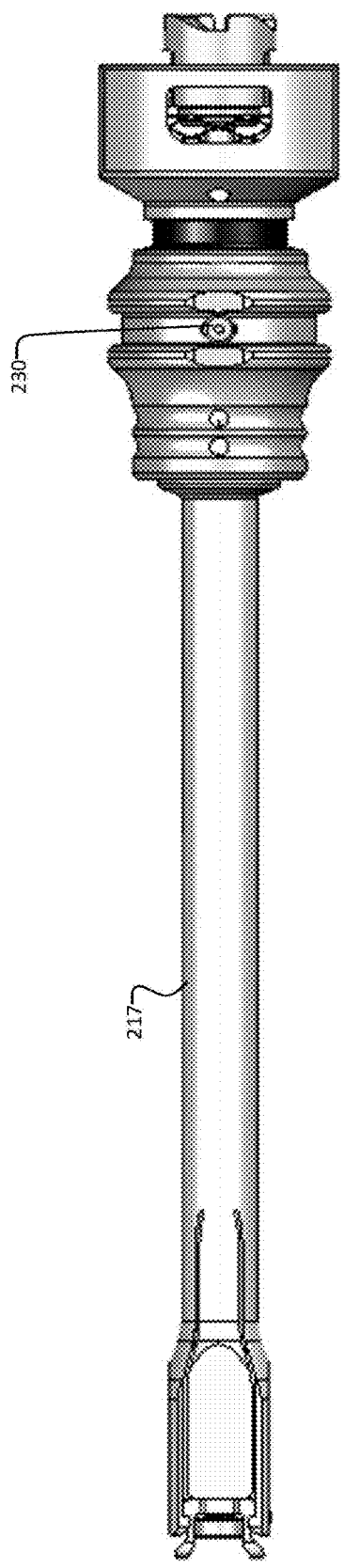
FIG. 8A is an example side view of the second component of FIG. 6.
Figure 8B:
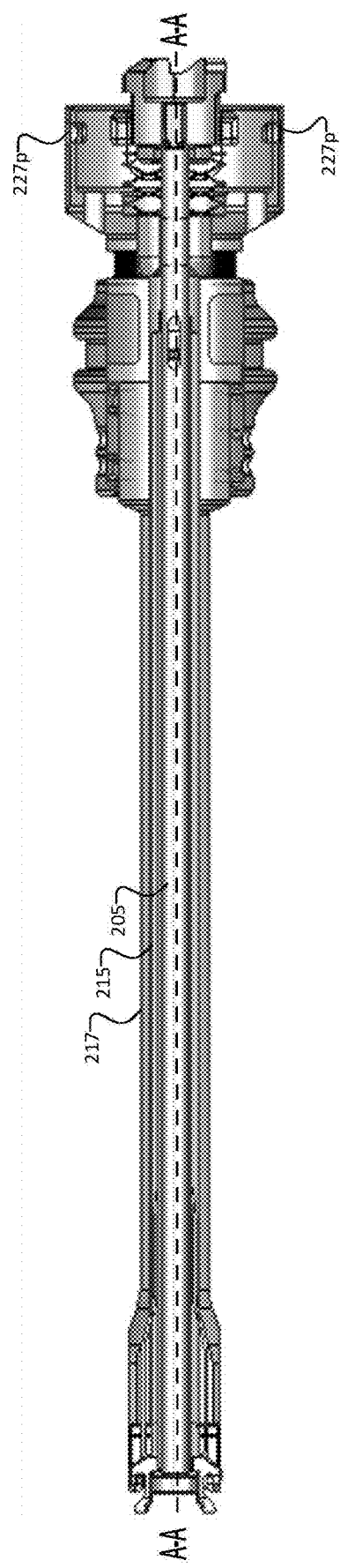
FIG. 8B is an example cross section view of the second component of FIG. 8A.

Referring generally to FIGS. 6-8B various example views of a second component 200 of a surgical instrument 1000 are illustrated. FIG. 6 is an example perspective view of a second component 200 and FIG. 7 is an example exploded parts view of the second component of FIG. 6. FIG. 8A is an example side view of the second component of FIG. 6 and FIG. 8B is an example cross section view of the second component 200. Second component 200 may have a proximal end 200p and a distal end 200d, for example. Second component 200 may include an outer shaft 217 defining an outside surface, at least partly, of second component 200, for example. Outer shaft 217 may include a hollow interior configured to receive inner shaft 215. For example, outer shaft 217 may surround inner shaft 215, at least partly. Inner shaft 215 may include a hollow interior configured to receive plunger 205. For example, inner shaft 215 may surround plunger 205, at least partly. In this way, the outer shaft 217 may surround the inner shaft 215 which in turn surrounds the plunger 205. Additionally, in various embodiments the outer shaft 217 and plunger 205 may move forward and backward linearly with respect to inner shaft 215. For example, inner shaft 215 may be fixed relative to outer shaft 217 and plunger 205.

Second component 200 may include a resilient coupler 219. Resilient coupler 219 may include an aperture 219a configured to receive a cross pin 230 (see FIGS. 8A and 9), for example. Cross pin 230 may be configured to operably couple the outer shaft 217, inner shaft 215, and plunger 205 such that plunger 205 may be linearly translatable forward and backward along axis A-A. For example, cross pin 230 may extend through a slotted aperture 217a of outer shaft 217, a circular aperture 215a of inner shaft, and a slotted aperture 205a of plunger 205. Resilient coupler 219 may cover or otherwise house a biasing member 221 therein, for example. Biasing member 221 may be a coil spring, an elastomeric material, a compressible foam, or the like. In various embodiments, resilient coupler 219 may be deformable and configured to compress, at least partly. For example, when securing a receiver 10 to a fastener 20 (also referred to as a bone screw). Resilient coupler 219 may surround or cover biasing member 221, for example, and biasing member 221 may apply a biasing force that urges resilient coupler 219 towards a non-compressed state, for example. In various embodiments, resilient coupler 219 may couple to the outer shaft 217, inner shaft 215 and plunger 205 in various ways. For example, pins, screws, etc. may alternately disposed in addition or in alternative to cross pin 230.

The plunger 205 may be disposed within the inner shaft 215 such that it can move linearly in opposing directions therein, but is prevented from rotating. In this regard, it should be understood that the proximal end of the plunger 205 may be able to slide within an interior space of the inner shaft 215. In various embodiments, a proximal end of the inner shaft 215 may comprise an aperture 215a having a size and shape generally corresponding to a cross sectional shape of cross pin 230. Additionally, in various embodiments, a proximal end of outer shaft 217 may comprise a slotted aperture 217a and a proximal end of plunger 205 may comprise a slotted aperture 205a. Furthermore, cross pin 230 may extend laterally through resilient coupler 219 and apertures 217a, 215a, and 205a. Because aperture 215a generally corresponds to the cross sectional shape of cross pin 230 and apertures 217a and 205a are slotted, cross pin 230 may fix inner shaft 215 relative to outer shaft 217 and plunger 205, for example. However, it should be understood that outer shaft 217 and plunger 205 may move linearly in a longitudinal direction because apertures 217a and 205a are slotted, i.e., they extend longitudinally for a greater distance than a cross sectional width of cross pin 230.

Outer shaft 217 may include an outer receiver interface 225 and inner shaft 215 may include an inner receiver interface 223. Plunger 205 may include a planar circular tip portion 213, for example. In other embodiments, tip portion 213 may be square, pointed, or non-planar. Tip portion 213 may be designed for the particular type of head assembly 1. The second component 200 may be configured to securely connect to an outside of receiver 10, via outer receiver interface 225 and inner receiver interface 223, as will be explained in further detail below. Furthermore, while second component 200 is secured to receiver 10, the tip portion 213 of plunger 205 may linearly translate forward and backward with respect to surgical instrument 1000 to secure the head assembly 1.

Outer shaft 217 may include a connecting cup 227 having a pair of apertures extending through side surfaces thereof, for example. Connecting cup 227 may be sized to receive connecting tip 127 of first component 100. For example, connecting tip 127 of first component 100 may be inserted into an interior of connecting cup 227 and connecting bars 128 may securely couple the connecting tip 127 (see FIG. 5A) to the connecting cup 227, for example. Connecting bars 128 may comprise a spring loaded depressible button, for example, that is configured to securely connect first component 100 to second component 200 by extending through apertures 227a of the connecting cup 227. In alternative embodiments, first component 100 and second component 200 may be removably coupled to one another by other means, such as, for example, a threaded interface. Additionally, in some embodiments connecting cup 227 may include a pair of inwardly extending protrusions 227p that may mate with corresponding channels 130 (see FIGS. 10 and 11). Channels 130 may extend longitudinally along an outside surface of connecting tip 127 and generally correspond in size and shape to inwardly extending protrusions 227p. Consistent with the above disclosure, first and second components 100 and 200 may securely couple to one another such that they will not separate during use. At least one advantage of surgical instrument 1000 is that first component 100 and second component 200 may be disconnected from one another. This may enable an end user to inspect the various interior components described herein and/or to clean them.

Figure 9:
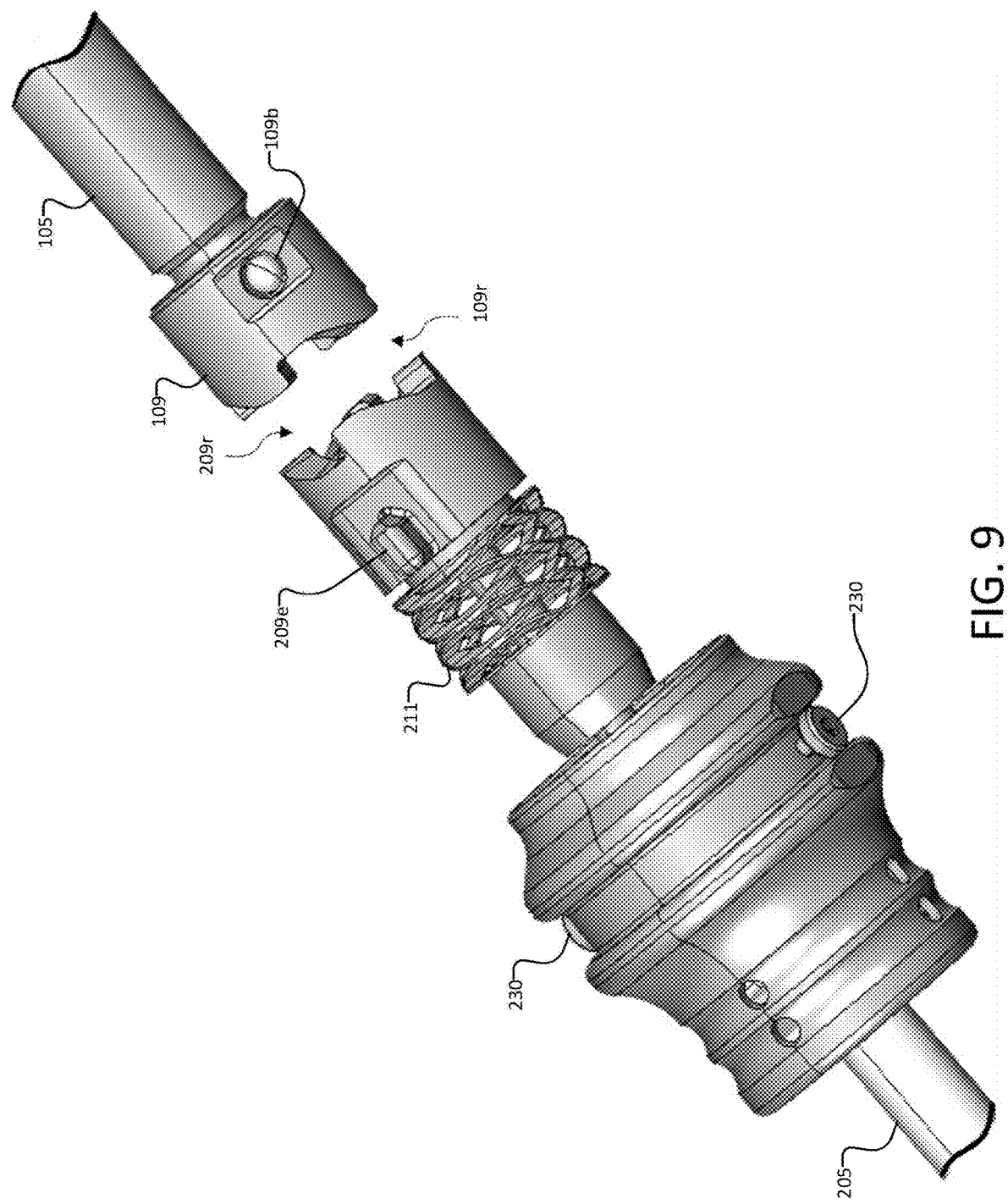
FIG. 9 is an example illustration with parts removed of a rotatable driver and a linear driver.

Referring generally to FIGS. 9-14 various example views of co-related components and interfaces between first component 100 and second component 200 are shown. FIG. 9 is an example illustration with parts removed of a rotatable drive shaft 105 positioned proximate plunger 205 to showcase how they mate with one another. However, it shall be understood that rotatable drive shaft 105 and plunger 205 are shown in a non mated position for ease of understanding and explanation. In the example embodiment, rotatable drive shaft 105 may include a positioning ball 109b extending laterally from a side surface of first mating end 109. Plunger 205 may include a corresponding second mating end 209, for example. First mating end 109 and second mating end 109 may generally correspond to one another in size, shape, and the various attributes of their contoured surface, as will be explained in further detail below. Second mating end 209 may include a pair of lateral protrusions 209e (may also be referred to as ears) extending laterally from a sidewall of second mating end 209, for example.

Plunger 205 may include a biasing element 211 that urges second mating end 209 towards first mating end 109, for example. The biasing element 211 provides a means to cause the plunger 205 to automatically and periodically return to being in direct contact with ramps 109r and 209r of the mating ends 109 and 209. Biasing element 211 may be a spring like webbing as illustrated, for example. In other embodiments, biasing element 211 may be a compressible spring such as a coil spring or the like. In other embodiments still, biasing element 211 may be a compressible foam, a piece of rubber, or the like. As explained above, in various embodiments, resilient coupler 219 may couple to the outer shaft 217, inner shaft 215 and plunger 205. Additionally, because cross pin 230 extends through each of the outer shaft 217, inner shaft 215, and plunger 205 the plunger 205 may be urged towards the proximal end 1000p of the surgical device.

The rotatable drive shaft 105 also comprises a first mating end 109 that is configured to mate with a corresponding second mating end 209 of plunger 205. Mating ends 109 and 209 may comprise shaped surfaces which engage each other so that rotation of drive shaft 105 in the clockwise direction (or alternatively in a counter clockwise direction) causes linear translation of the plunger 205 forward along axis A-A and biasing element 211 causes linear translation of the plunger 205 backward along axis A-A. In this regard, mating end 109 comprises a first plurality of ramps 109r and second mating end 209 comprises a second plurality of ramps 209r. For example, ramps 109r of first mating end 109 may be defined by a peak 109p and a valley 109v. Similarly, ramps 209r of second mating end 209 may be defined by a peak 209p and a valley 209v. Peaks 109p and 209p may include a flat surface extending perpendicular to axis A-A and a curved surface projecting towards valleys 109v and 209v, respectively. Each valley 109v, and 209v may include a flat run out portion including a flat surface extending in a direction that is perpendicular to axis A-A, for example. Each valley 109v, and 209v may also include a sidewall that extends from the flat run out portion to the peak 109p and 209p of an adjacent ramp, respectively, in a direction that is parallel with axis A-A, for example. In various embodiments, the flat run out portion of each valley 109v and 209v may correspond generally in size, shape, and orientation to the flat portion of peaks 109p and 209p. In the disclosed embodiment, first mating end 109 and second mating end 209 each comprise four ramps, however other embodiments may have more or less ramps. For example, about 2-6 ramps.

Figure 10:
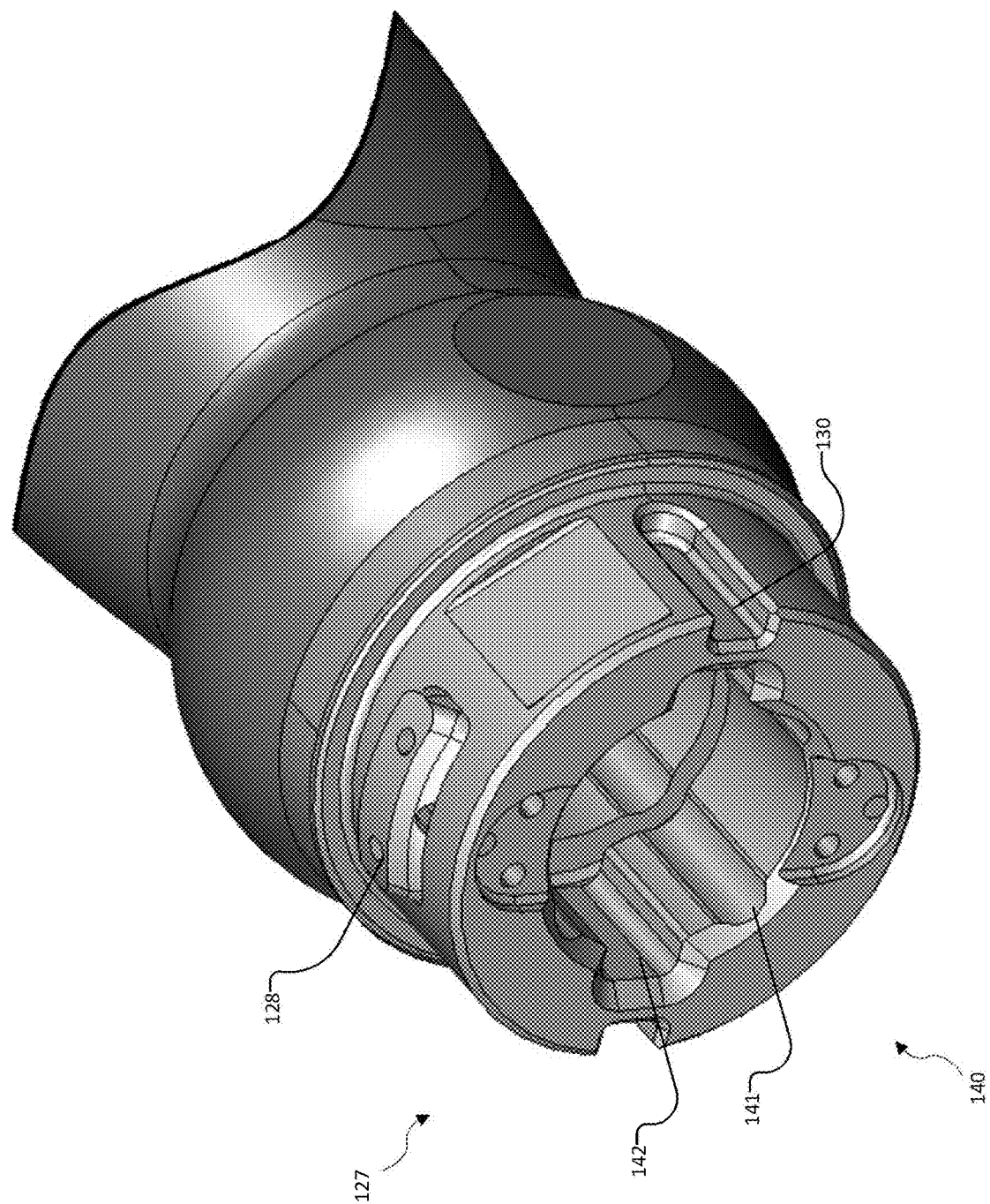
FIG. 10 is an example perspective view of a distal end of the first component of the modular surgical instrument.
Figure 11:
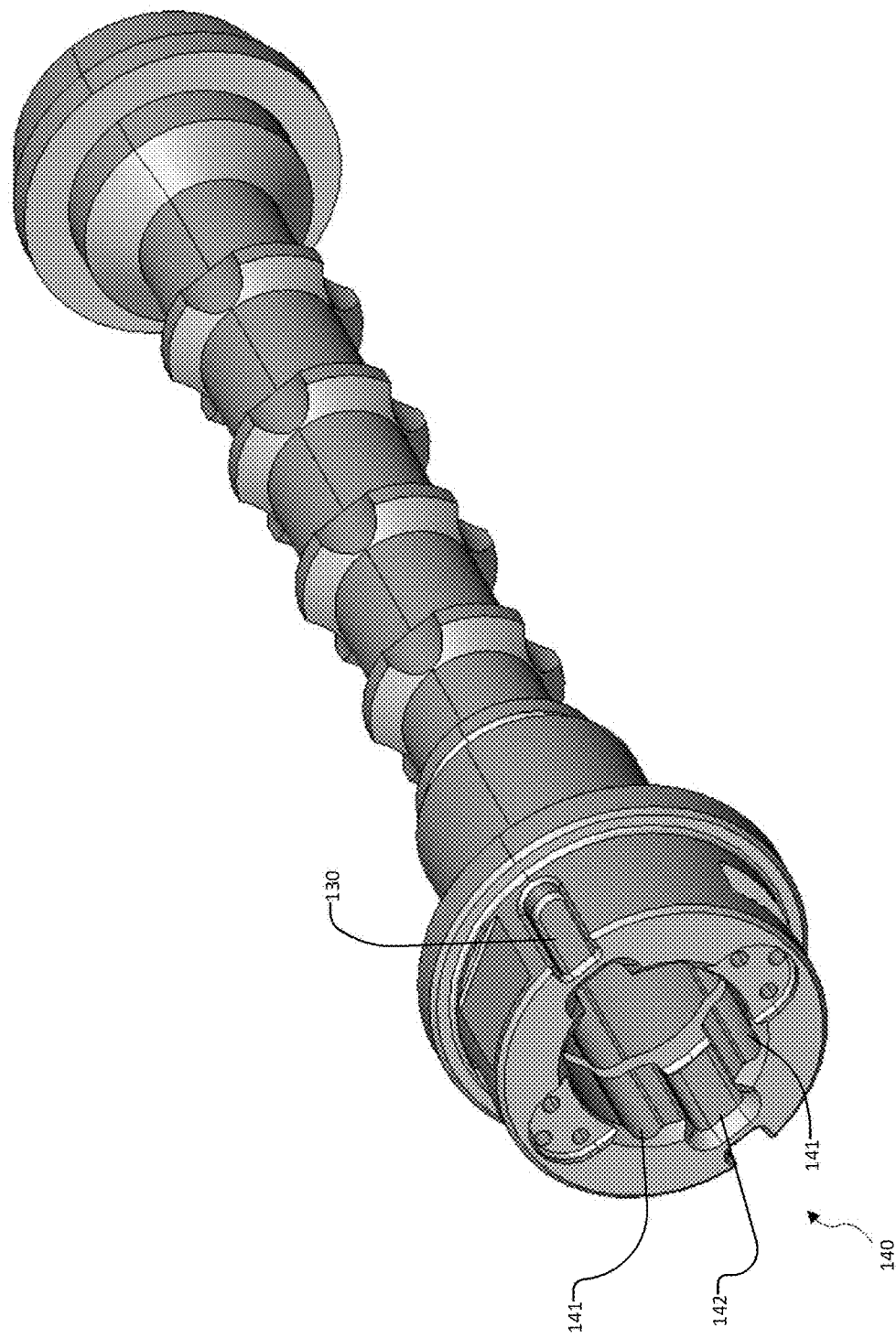
FIG. 11 is an example perspective view of a housing shaft of the first component of the modular surgical instrument.
Figure 12:
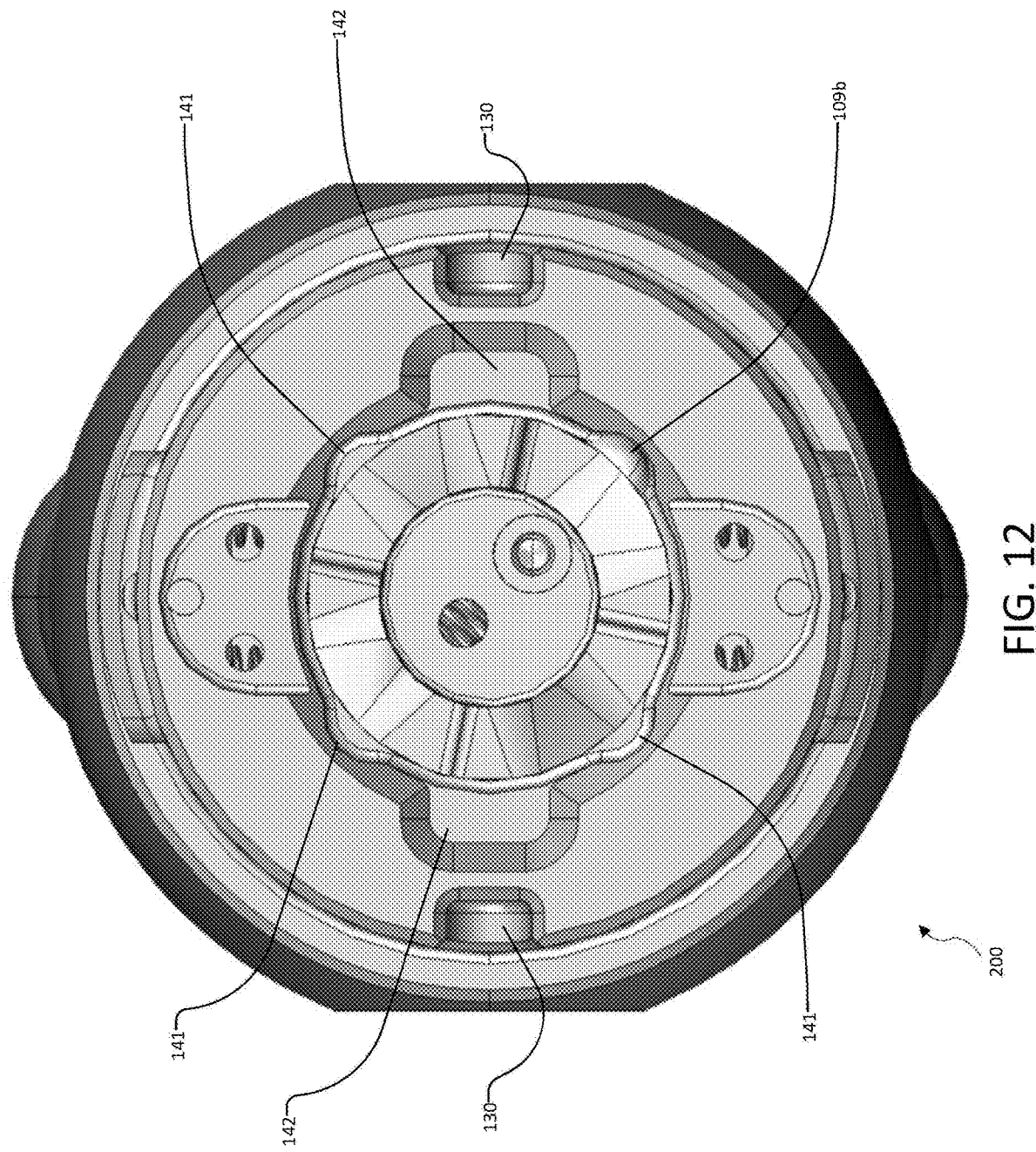
FIG. 12 is a top down view of the distal end of the first component of the modular surgical instrument.

FIG. 10 is an example perspective view of a distal end of the first component 100 and FIG. 11 is an example perspective view of a drive housing 110 of the first component 100. FIG. 12 is a top down view of the interior of the drive housing 110. FIG. 13 is a perspective view of a first mating end 109 of rotatable drive shaft 105 and FIG. 14 is a perspective view of a second mating end 209 of plunger 205.

In the example embodiment, a distal end of the drive housing 110 may include a contoured interior 140 where first mating end 109 and second mating end 209 come into contact with one another. Contoured interior 140 may include a number of geometrical features relevant to the transfer of forces and operation of surgical instrument 1000, for example. The contoured interior 140 may include a pair of channels 142 that generally correspond in size and shape to protrusions 209e. Channels 142 may extend longitudinally and surround and/or otherwise confine protrusions 209e therein such that plunger 205 is prevented from rotating. For example, when drive shaft 105 is rotating and mating ends 109 and 209 are in direct contact, channels 142 may prevent plunger 205 from rotating. Additionally, protrusions 209e may slide forward and backward within channels 142 such that the rotational force of drive shaft 105 is transferred into linear movement of plunger 205 due to the sliding engagement of mating ends 109 and 209. For example mating end 109 may rotate and slide across mating end 209 (which does not rotate) thereby translating the rotational movement of mating end 109 into linear movement of mating end 209, for example. In various embodiments, the extent of the linear movement may correspond to a distance between a corresponding peak 109p and valley 109v, for example Contoured interior 140 may also include at least one groove 141. In the example embodiment, four grooves 141 are provided that extend longitudinally along the interior of drive housing 110. The four grooves 141 may be symmetrically disposed radially around the interior of drive housing 110, for example (see FIG. 12). In various embodiments, the radial positioning of grooves 141 may correspond to the radial positioning of ramps 109r and 209r, for example. Accordingly, in embodiments with more or less ramps 109r and 209r a corresponding number of grooves 141 may be provided that are radially disposed in a corresponding geometrical orientation. Grooves 141 may comprise curved surfaces having a size and shape that generally corresponds to positioning ball 109b, for example. Positioning ball 109b may be biased outwardly by a positing spring (not illustrated) thereby enabling positioning ball 109b to move laterally with respect to first mating end 109. Accordingly, positioning ball 109b may be selectively seated in any one of grooves 141. Moreover, when positioning ball 109b is seated in any one of grooves 141 peaks 109p of ramps 109r are aligned with valleys 209v of ramps 209r, for example. At least one advantage of including positioning ball 109b and four symmetrically disposed corresponding grooves 141 may be that rotatable drive shaft 105 is naturally rotated into a position where ramps 109r are meshed with ramps 209r. This may be particular advantageous because without these features rotatable drive shaft 105 may be rotated and stopped in a position where ramps 109r would not otherwise be meshed properly with ramps 209r. If such a scenario were to occur, excess wear and tear on mating ends 109 and 209 may occur and/or an end user may experience a negative feedback or a jolt of force when the ramps do become engaged. In this way, the contoured interior and positioning ball are configured to align and/or mesh ramps 109r with ramps 209r.

Referring generally to FIGS. 15-18 various views of a distal end 1000d of surgical instrument 1000 are shown. For example, FIGS. 15-18 further illustrate various attributes of the outer receiver interface 225 and inner receiver interface 223. The outer receiver interface 225 may include a pair of flexible arms 225a. For example a first flexible arm 225a may be disposed opposite a second flexible arm 225a.

Flexible arms 225a may define a recess therebetween. The recess defined by the flexible arms 225a may be configured to have a size and shape to receive a portion of an external object (e.g., a receiver 10 of FIG. 2) during a medical procedure (e.g., the placement of an implant in a patient). The flexible arms 225a may be formed of a rigid material, such as metal for example or a semi rigid material. The flexible arms 225a may be configured to bend in and out laterally with respect to axis A-A of surgical instrument 1000 due to, e.g., seams 217s. Seams 217s may extend longitudinally along outer shaft 217 on side surfaces of receiver interface between flexible arms 225a, for example. Additionally or alternatively, in some embodiments, the flexible arms 225a may be formed of the same material as the remaining portion of outer shaft 217, but have a relatively smaller thicknesses allowing the flexible arms 225a to be bendable.

In the example embodiment, a distal tip of each flexible arm 225a includes an elongated aperture 225c and an inwardly extending platform 225b. In various embodiments an elongated aperture 225c may be disposed adjacent each inwardly extending platform 225b. Inwardly extending platform 225b may have a size and shape generally corresponding to a connecting portion 11a (chamfered detent) of receiver 10, for example. The particular shape of the inwardly extending platform 225b may correspond to the particular shape of a corresponding detent and/or hook portion, (e.g., connecting portion 11a). For example, inwardly extending platform 225b may be configured to interface with a different style of head assembly 1 than shown in FIG. 2, e.g., a head assembly of a uniaxial screw, a head assembly of a multiaxial screw (MAS), a head assembly of a reduction head multiaxial screw (RMAS), or a head assembly of an extended tab MAS. In this way, the inwardly extending platform 225b and connecting portion 11a of receiver 10 may provide a way to quickly couple the surgical instrument 1000 by placing the flexible arms 225a over a receiver 10 and engaging them together, as will be explained in further detail below.

In the example embodiment, the inner receiver interface 223 may include a hook 223a and a sloped surface 223b defining therebetween a recess configured to mate with the distal tip of flexible arm 225a, for example. As illustrated, the hook 223a is a "c" shaped hook that is mated with the distal tip end of flexible arm 225a by passing through aperture 225c. For example, the hook 223a extends laterally away from axis A-A and is engaged with the distal tip end of flexible arm 225a on the outside surface and inner surface thereof. When each hook 223a is engaged with each flexible arm 225a—the flexible arms 225a may become secured and/or rigid, i.e., no longer flexible in that they will not bow outwards with respect to axis A-A, for example. For example, each hook 223a may selectively couple to a corresponding flexible arm 225a in a locked position, for example. Accordingly, each hook 223a may be configured to rigidly secure each flexible arm 225a to the receiver 10 such that the receiver 10 is fixedly secured to the outer shaft 217 and inner shaft 215 at the distal end 1000d of the surgical instrument 1000.

The inner receiver interface 223 may also include a sloped surface 223b. Sloped surface 223b may extend laterally away from the proximal end 1000p and axis A-A at an angle. In various embodiments, the angle may range from about 15 degrees to about 75 degrees, about 25 degrees to about 65 degrees, about 35 degrees to about 55 degrees, and or about 45 degrees, for example. Sloped surface 223b may serve the purpose of providing a slanted surface that spreads the flexible arms 225a outwardly to disconnect from receiver 10. For example, in practice a surgeon move slide the outer shaft 217 downward (e.g., in a distal direction towards distal end 1000d) thereby pushing a distal most end of flexible arm 225a against the sloped surface 223b which naturally inclines or urges the flexible arm 225a laterally outward by a degree corresponding to the angle of sloped surface 223b. In this way, the sloped surfaces 223b may be configured to provide a bearing surface that causes flexible arms 225a to bow outward and release (or connect to) for connecting outer receiver interface 225 to a receiver 10.

Figure 15:
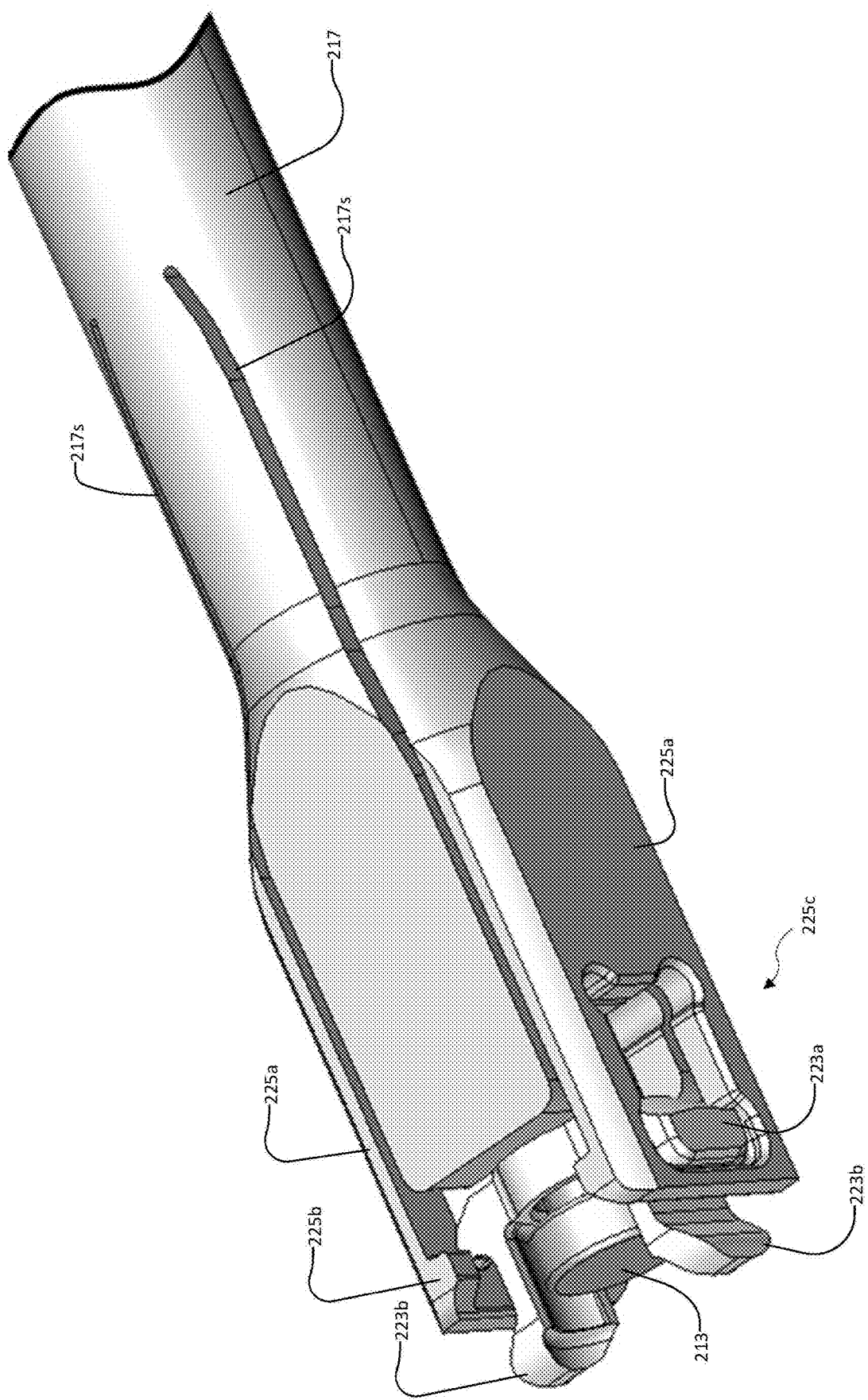
FIG. 15 is a perspective view of a distal tip of the second component.
Figure 16:
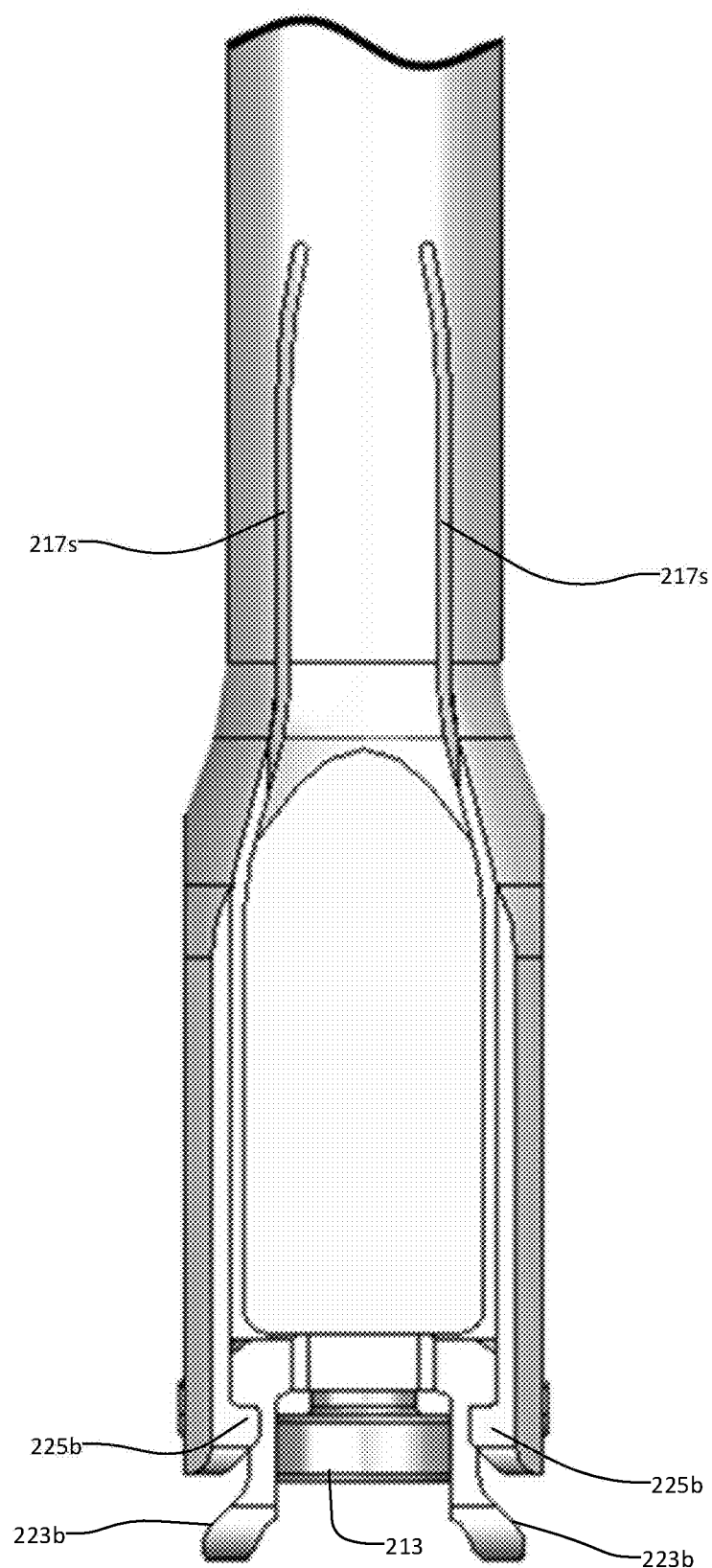
FIG. 16 is a front view of the distal tip of the second component.
Figure 17:
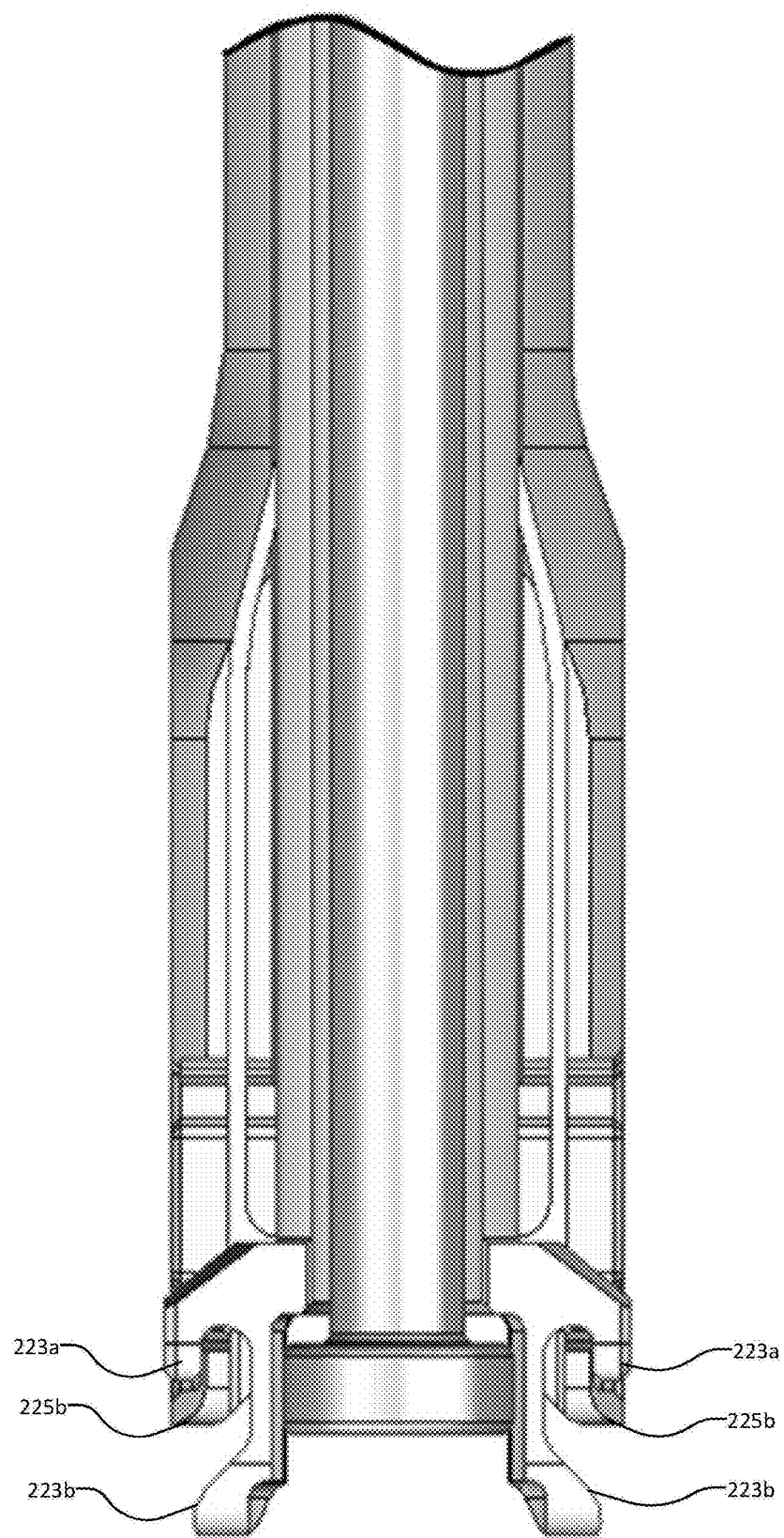
FIG. 17 is a cross section of the distal tip of the second component.
Figure 18:
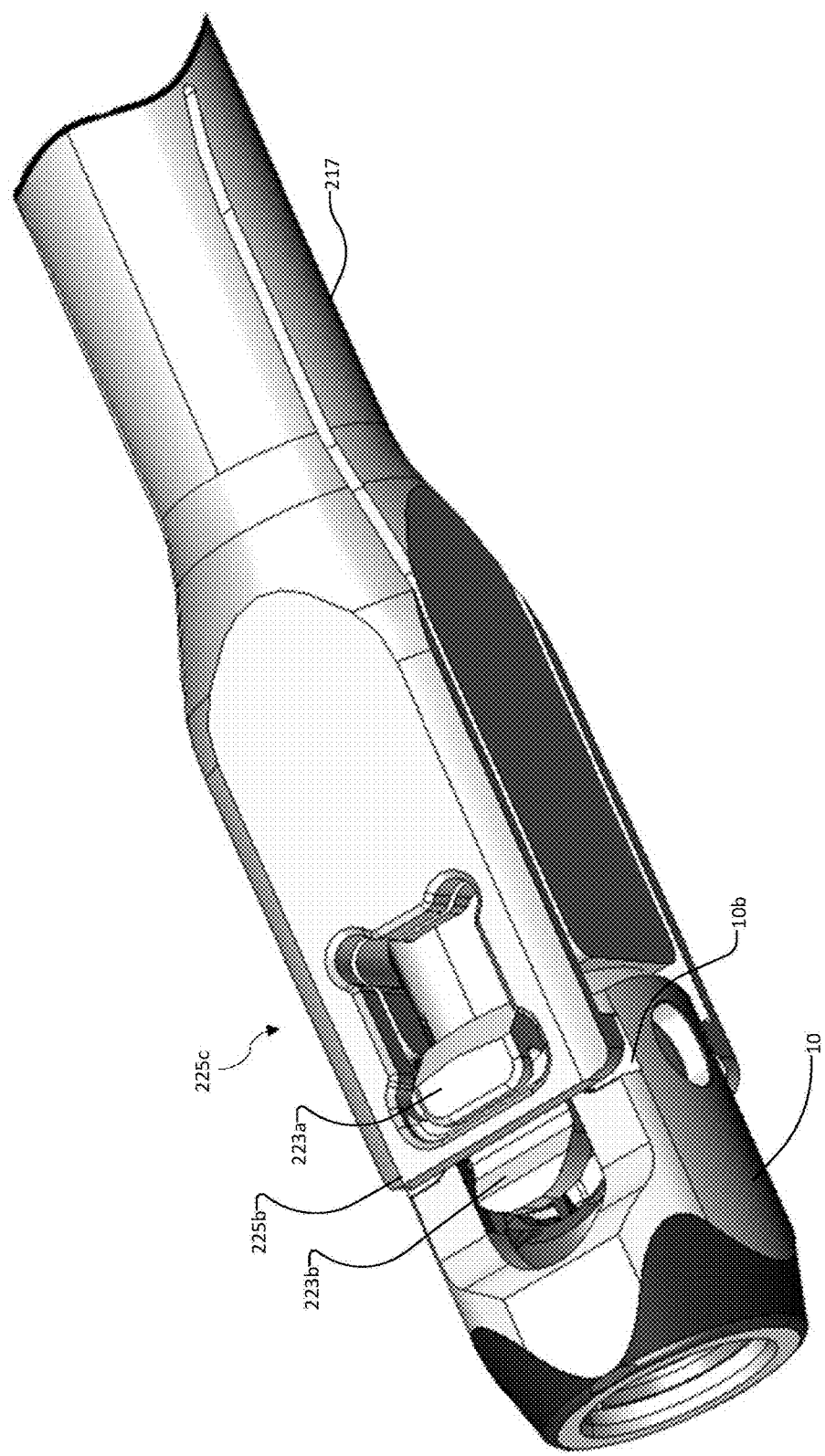
FIG. 18 is a perspective view of the distal tip of the second component coupled to a receiver.

In various embodiments, the outer shaft 217 can be locked in positon via a mechanical lock mechanism (not shown) once it reaches an engaged position (e.g., shown in FIG. 15). The mechanical lock mechanism can include, but is not limited to, a latch, and/or a depressible button disposed on the outer shaft 217 that extends through a through hole of the inner shaft 215, for example, when aligned therewith. In the locked position, the relative position of the outer shaft 217 to the inner shaft 215 may be fixed (at least with respect to one another) and outer receiver interface 225 and inner receiver interface 223 may not become disengaged. However, it should be understood that plunger 205 may still be able to move forward and backwards along axis A-A within an interior of inner shaft 215, for example.

Referring generally to FIGS. 19A-20B various views of the outer receiver interface 225 and inner receiver interface 223 are shown while coupled to a corresponding receiver 10. FIGS. 19A-19C show the outer receiver interface 225 and inner receiver interface 223 in an engaged position where they are securely coupled to a receiver 10. FIGS. 20A and 20B each show a cross section of the outer receiver interface 225 and inner receiver interface 223 while coupled to a corresponding receiver 10, for example. As illustrated, the hooks 223a extend perpendicular to a bearing surface of the inwardly extending platforms 225b and through the aperture 225c. The bearing surface of the inwardly extending platforms 225b is securely mated with the connecting portion 11a of the receiver, for example. The hook 223a and sloped surface 223b may each extend between arms 11 of receiver 10, for example.

In practice a surgeon may place surgical instrument 1000 in proximity to the receiver 10. The central axis A-A of the surgical instrument 1000 may be axially aligned with a central axis of the receiver 10 and fastener 20, for example. Once aligned, the surgical instrument 1000 may be moved in a direction towards the receiver 10. As a result of this movement, the receiver 10 may be received by surgical instrument 1000 at a distal end 1000d. The receiver arms 11 may slidingly engage the flexible arms 225a and urge the flexible arms 225a outward, at least partly. For example, this sliding engagement causes the flexible arms 225a to be respectively pushed out and away from the plunger 205 of surgical instrument 1000 in opposite directions. Once aligned, inwardly extending platform 225b of the flexible arms 225a may slide into and/or otherwise become mated or seated within connecting portion 11a, for example. Next the outer shaft 217 may be biased in a proximal direction towards proximal end 1000p by, e.g., biasing element 211, and/or biasing member 221. This biasing force may cause the hooks 223a to securely engage and/or lock with the flexible arms 225a such that the receiver 10 may not become uncoupled (at least while in the engaged position). As explained above, in the locked position, the inner receiver interface 223 prevents the outer receiver interface 225 from bending or bowing with respect to axis A-A. Additionally, this type of interface provides an easy means for a surgeon to visually verify that the receiver 10 is secured to the surgical instrument 1000 before operation.

Subsequently, an external instrument (e.g., drill or hand driver) may be coupled to rotatable drive end 101 provided at the proximal end 1000p of the surgical instrument 1000, as explained above. The external instrument can include, but is not limited to, a high-speed surgical drill. Next, an end user may depress a trigger or actuator of the external instrument so that torque is transferred from the external instrument to the rotatable drive shaft 105 of first component 100. This torque causes the rotatable drive shaft 105 to rotate relative to the handle 103. Consequently, first mating end 109 slides against second mating end 209 and due to the ramps 109r and 209r the plunger 205 may linearly advance forward along axis A-A in a distal direction. For example, this sliding engagement between first mating end 109 and second mating end 209 causes linear translational movement of plunger 205 along central axis A-A. As a result of this linear translation movement, the planar circular tip portion 213 comes in contact with crown 30 and applies a pushing force on crown 30.

The pushing force causes the crown 30 to move towards the fastener 20. In turn, the crown 30 applies a pushing force on an upper retainer 31. In effect, the upper retainer 31 is pushed by the crown 30 until the upper retainer 31 moves into a groove formed on an inner surface of the receiver 10, for example. Notably, the upper retainer 31 temporarily prevents a lower retainer 32 from moving into a second groove formed on an inner surface of the receiver 10. The lower retainer 32 and upper retainer 31 may be moved into their final positions after repetitive pushing force is applied to the crown by the plunger 205, for example as set forth in detail in U.S. patent application Ser. No. 16/830,377, titled Powered Modular Head Locker, the contents of which are incorporated herein in their entirety. After the lower retainer 32 is in its final position seated within the second groove, the receiver 10 is securely coupled to the fastener 20.

It should be noted that when an end user is not driving or otherwise rotating the rotatable drive shaft 105, the rotatable drive shaft 105 may be aligned into one of the four positions where the ramps 109r of first mating end 109 are aligned with the valleys 209v of second mating end 209 as explained above. For example, due to positioning ball 109b and the four grooves 141. Thereafter, an end user may resume rotation of the rotatable drive shaft 105 which causes first mating end 109 and second mating end 209 to directly contact each other and move plunger 205 forward linearly along axis A-A. It should be noted that throughout the rotation of rotatable drive shaft 105 biasing element 211 may resiliently bias and return the second mating end 209 back to being in direct contact with first mating end 109.

After the head assembly 1 is fully secured as explained above an end user may uncouple surgical instrument 1000 from receiver 10. For example, an end user may push outer shaft 217 and/or surgical instrument 1000 down against the secured head assembly 1. In doing so the flexible arms 225a may be pushed outward laterally by sloped surfaces 223b thereby uncoupling surgical instrument 1000 from receiver 10, for example. The surgical instrument 1000 may then be moved out and away from the receiver 10.

As evident from the above-discussion, the surgical instrument 1000 provides a means for quickly locking a receiver 10 to a fastener 20. Additionally, surgical instrument 1000 may also be used to insert the head assembly 1 into a surgical site of a patient also reducing the total surgery time and complications associated with using multiple surgical tools. For example, surgical instrument 1000 allows an end user to push down with the instrument on the head that is already disposed on the screw. This pressure causes the instrument to securely attach to the head. Then, the user can pull a power tool's trigger to spin an upper shaft part of the instrument. This causes ramped surface of the first mating end 109 and second mating end 209 to slidingly engage each other, whereby a linear translation of plunger 205 occurs. The linear translation of plunger 205 causes a pushing force to be applied to the crown for locking the head on the screw. To release the instrument from the head, the user only has to push surgical instrument 1000 down to uncouple from the receiver 10 and lift the surgical instrument 1000 up, for example.

Figure 21:
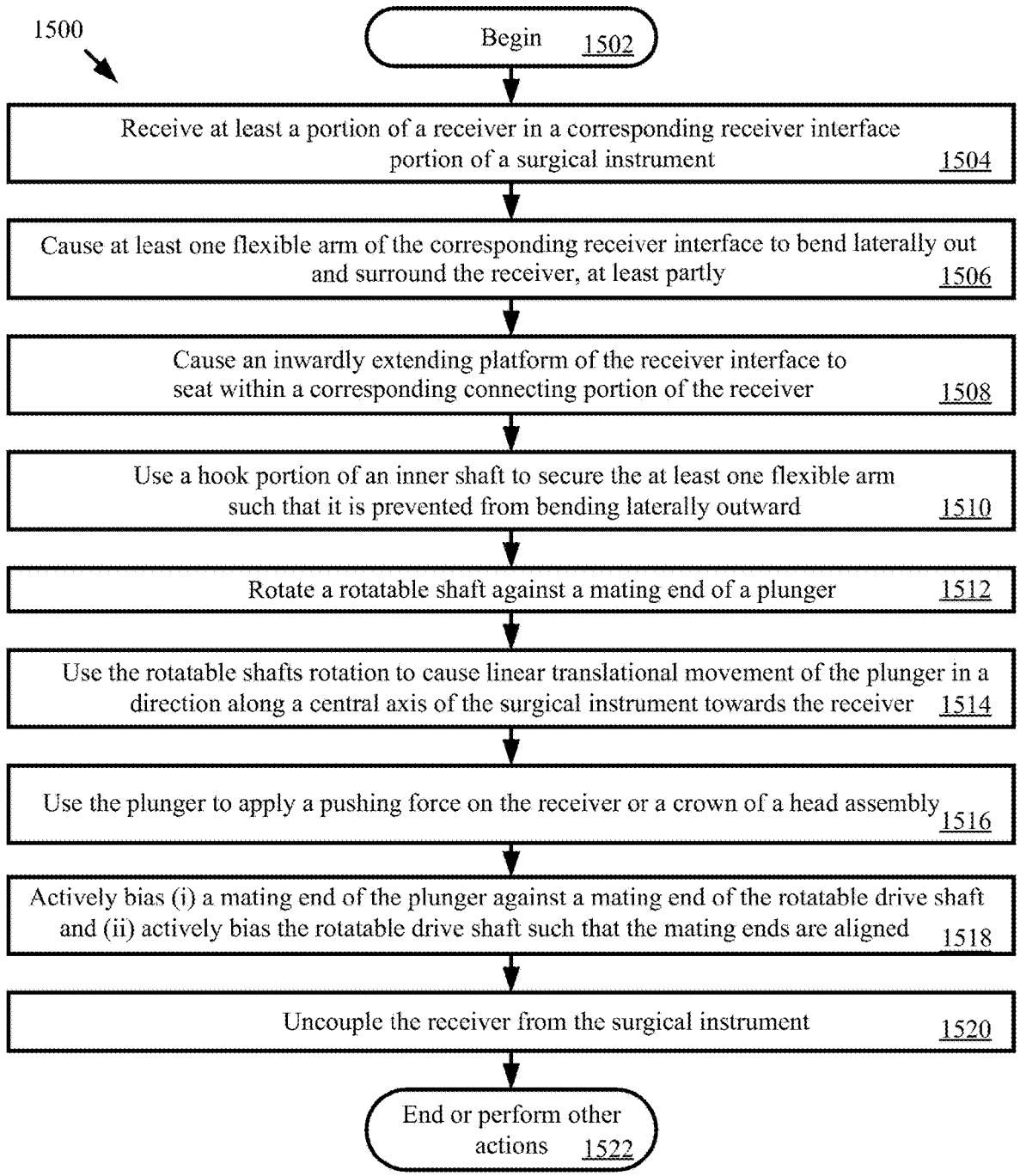
FIG. 21 is a flow diagram of a method of operation of a surgical instrument.

Referring now to FIG. 21, there is provided a flow diagram of an illustrative method 1500 for operating a surgical instrument (e.g., surgical instrument 1000) in a way that is consistent with the above disclosure. Method 1500 begins with step 1502 and continues with step 1504. At step 1502, an end user, via surgical instrument 1000, may receive at least a portion of a receiver in a corresponding receiver interface, for example. Next at step 1504, an end user may cause at least one flexible arm of the corresponding receiver interface to bend laterally out and surround the receiver, at least partly. Next, at step 1508, an end user may cause an inwardly extending platform of the receiver interface to seat within a corresponding connecting portion of the receiver, for example. Next, at step 1510 an end user may use a hook portion of an inner shaft to secure the at least one flexible arm such that it is prevented from bending laterally outward, for example. After the receiver is rigidly and securely coupled to surgical instrument 1000, an end user, at step 1512, may rotate a rotatable shaft against a mating end of a plunger, for example. In doing so, at step 1514 the end user may use the rotatable shafts rotation to cause linear translational movement of the plunger in a direction along a central axis of the surgical instrument towards the receiver, for example. Next, at step 1516, an end user may use the plunger to apply a pushing force on the receiver or a crown of a head assembly for example. Additionally, and throughout the process described above, at step 1518 the surgical instrument may continuously and actively bias (i) a mating end of the plunger against a mating end of the rotatable drive shaft and (ii) actively bias the rotatable drive shaft such that the mating ends of the rotatable drive shaft and plunger are aligned. Thereafter, at step 1520, an end user may uncouple the receiver from the surgical instrument. For example, by pushing down on the outer shaft the at least one flexible arm contacts a corresponding sloped surface of the inner shaft that urges the at least one flexible arm outward such that it may uncouple from the receiver. It should be noted that optionally, at step 1522 an end user may perform additional actions consistent with the disclosure herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A surgical instrument, comprising:
 a drive shaft axially aligned with a central axis of the surgical instrument, the drive shaft including a first mating end and being rotatably supported within a drive housing, the drive housing supporting the first mating end;
 an outer shaft including an outer receiver interface configured to selectively couple and uncouple to a connecting portion of a receiver;
 a plunger, the plunger being axially aligned with the central axis of the surgical instrument and including a second mating end disposed within the drive housing, the second mating end being axially aligned with and in contact with the first mating end; and
 a biasing member configured to urge the second mating end of the plunger into contact with the first mating end of the drive shaft;
 wherein the plunger is configured to linearly translate forward and backward along the central axis upon rotation of the drive shaft around the central axis,
 wherein:
 the drive housing comprises a contoured interior supporting the first mating end, the second mating end being disposed within the contoured interior, the contoured interior comprises a plurality of grooves extending in a direction parallel with the central axis,
 the first mating end comprises a first plurality of ramps having a first plurality of peaks and a first plurality of valleys and the second mating end comprises a second plurality of ramps having a second plurality of peaks and a second plurality of valleys,
 the first mating end comprises a positioning ball extending laterally from a side surface of the first mating end in a direction perpendicular to the central axis, the positioning ball being selectively seated within one groove of the plurality of grooves, and
 the positioning ball is configured to align the first plurality of ramps with the second plurality of ramps such that the first plurality of peaks is aligned with the second plurality of valleys and the first plurality of valleys is aligned with the second plurality of peaks.

2. The surgical instrument according to claim 1, wherein the outer shaft comprises at least one flexible arm, the at least one flexible arm being configured to bow laterally outward with respect to the central axis to facilitate selectively coupling and uncoupling with the connecting portion of the receiver.

3. The surgical instrument according to claim 2, comprising:
 an inner shaft disposed within the outer shaft, at least partly, the inner shaft including an inner receiver interface configured to selectively couple and uncouple from the outer receiver interface, and
 wherein when the inner receiver interface is coupled with the outer receiver interface.

4. The surgical instrument according to claim 1, wherein:
 a distal end of the outer shaft comprises a first flexible arm and a second flexible arm disposed opposite the first flexible arm, the first flexible arm including a first platform and the second flexible arm including a second platform,
 the first flexible arm and the second flexible arm defining a recess between the first flexible arm and the second flexible arm,
 the first flexible arm and the second flexible arm each being configured to bow laterally outward with respect to the central axis to thereby widen the recess and facilitate selectively coupling and uncoupling with the connecting portion of the receiver,
 the connecting portion of the receiver comprises a first detent and a second detent, and the first platform and the second platform being configured to mate with the first detent and the second detent, respectively.

5. The surgical instrument according to claim 4, comprising:
an inner shaft disposed at least in part within the outer shaft, a distal end of the inner shaft including an inner receiver interface including a first hook and a second hook, the first hook being configured to couple to the first flexible arm and the second hook being configured to couple to the second flexible arm in a locked position, and
wherein, in the locked position, the first flexible arm and the second flexible arm are prevented from bowing laterally outward with respect to the central axis.

6. The surgical instrument according to claim 5, wherein:
a tip of the inner receiver interface includes a first sloped surface and a second sloped surface, the first sloped surface and the second sloped surface each extending away from and being angled with respect to the central axis,
the outer shaft is movable forward and backward along the central axis with respect to the inner shaft, and
the outer shaft is configured to slide forward along the central axis such that the first flexible arm contacts the first sloped surface and the second flexible arm contacts the second sloped surface thereby causing the first flexible arm and the second flexible arm to bow outward with respect to the central axis.

7. A method for operating a surgical instrument, comprising:
receiving at least a portion of a receiver in a corresponding receiver interface of a surgical instrument;
rotating a drive shaft having a first mating end against a second mating end of a plunger, wherein the first mating end comprising a first plurality of ramps having a first plurality of peaks and a first plurality of valleys and the second mating end comprising a second plurality of ramps having a second plurality of peaks and a second plurality of valleys;
linearly translating the plunger in a first direction towards the receiver;
applying a pushing force on the receiver via the plunger; and
biasing the plunger in a second direction towards the drive shaft;
urging the second mating end of the plunger into contact with the first mating end of the drive shaft;
wherein the first mating end comprises a positioning ball extending laterally from a side surface of the first mating end in a direction perpendicular to a central axis of the surgical instrument, the positioning ball being selectively seated within one groove of a plurality of grooves of a contoured interior of a drive housing, the plurality of grooves extending in a direction parallel with the central axis; and
wherein the positioning ball is configured to align the first plurality of ramps with the second plurality of ramps such that the first plurality of peaks is aligned with the second plurality of valleys and the first plurality of valleys is aligned with the second plurality of peaks.

8. The method according to claim 7, comprising:
bending at least one flexible arm of the corresponding receiver interface laterally outward with respect to a central axis of the surgical instrument such that the at least one flexible arm surrounds the receiver, at least partly.

9. The method according to claim 8, comprising:
mating an inwardly extending platform of the at least one flexible arm within a connecting portion of the receiver, the connecting portion having a size and shape generally corresponding to the inwardly extending platform.

10. The method according to claim 9, comprising:
securing the at least one flexible arm with a hook portion of an inner shaft thereby preventing the at least one flexible arm from bending laterally outward.

11. The method according to claim 1, comprising:
securing the at least one flexible arm to the receiver after the mating the inwardly extending platform step.

12. The method according to claim 9, comprising:
biasing the mating end of the plunger against the mating end of the rotatable drive shaft.

13. The method according to claim 12, comprising:
biasing the drive shaft such that the mating end of the drive shaft is properly aligned with the mating end of the plunger.

14. The method according to claim 12, comprising:
uncoupling the receiver from the surgical instrument by pushing down on an outer shaft of the surgical instrument such that the at least one flexible arm contacts a sloped surface of an inner shaft of the surgical instrument, the sloped surface urging the at least one flexible arm outward and away from the receiver.

15. The method according to claim 7, wherein the linearly translating the plunger in a first direction step is caused by a sliding engagement between ramped surfaces of the mating end of the plunger and ramped surfaces of the mating end of the drive shaft.

16. The method according to claim 7, comprising:
seating the positioning ball within the groove of the plurality of grooves having a size and shape generally corresponding to the positioning ball; and
biasing the drive shaft into alignment with the plunger such that first plurality of peaks of the mating end of the drive shaft are aligned with the second plurality of valleys of the mating end of the plunger.

17. A modular surgical instrument for fixing a receiver to a bone screw, comprising:
a first component configured to selectively couple and uncouple with a second component, the first component and second component defining a central axis of a surgical instrument having a distal end and a proximal end;
the first component comprising:
a drive shaft axially aligned with the central axis of the surgical instrument, the drive shaft including a first mating end and being rotatably supported within a drive housing, the drive housing including a contoured interior supporting the first mating end;
the second component comprising:
an outer shaft including an outer receiver interface disposed at the distal end, the outer receiver interface having a first flexible arm and a second flexible arm defining a recess configured to receive the receiver, the first flexible arm and second flexible arm being configured to selectively couple and uncouple to a connecting portion of the receiver by bowing laterally outward with respect to the central axis and enlarging the recess;
an inner shaft disposed within the outer shaft, at least partly, the inner shaft including an inner receiver interface disposed at the distal end and having a first hook and a second hook, the first hook being configured to couple to the first flexible arm and the second hook being configured to couple to the second flexible arm in a locked position; and a plunger, the plunger being axially aligned with the central axis of the surgical instrument and including a second mating end disposed within the countered interior of the drive housing, the second mating end being aligned with and in contact with the first mating end; and a biasing member configured to urge the second mating end of the plunger into contact with the first mating end of the drive shaft;

wherein the plunger is configured to linearly translate forward and backward along the central axis upon rotation of the drive shaft around the central axis; and wherein:

the first mating end comprises a first plurality of ramps having a first plurality of peaks and a first plurality of valleys and the second mating end comprises a second plurality of ramps having a first plurality of peaks and a second plurality of valleys, the contoured interior comprises a plurality of grooves extending in a direction parallel with the central axis, the first mating end comprises a positioning ball extending laterally from a side surface of the first mating end in a direction perpendicular to the central axis, and the positioning ball is selectively seated within one groove of the plurality of grooves and is configured to align the first plurality of peaks with the second plurality of valleys and the first plurality of valleys with the second plurality of peaks.

* * * * *